United States Patent [19]
Riddell et al.

[11] Patent Number: 5,827,642
[45] Date of Patent: Oct. 27, 1998

[54] RAPID EXPANSION METHOD ("REM") FOR IN VITRO PROPAGATION OF T LYMPHOCYTES

[75] Inventors: Stanley R. Riddell, Bothell; Philip D. Greenberg, Mercer Island, both of Wash.

[73] Assignee: Fred Hutchinson Cancer Research Center, Seattle, Wash.

[21] Appl. No.: 317,100

[22] Filed: Oct. 3, 1994

Related U.S. Application Data

[63] Continuation of Ser. No. 299,930, Aug. 31, 1994, abandoned.
[51] Int. Cl.$^6$ .............................. C12N 5/02; C12N 5/08; A01N 1/02; A61K 35/12
[52] U.S. Cl. .................... 435/2; 435/372.3; 435/373; 435/375; 435/383; 435/386; 435/384; 424/93.71
[58] Field of Search .............................. 424/93.71; 435/2, 435/240.1, 240.2, 240.21, 240.25, 372.3, 373, 375, 383, 386, 384; 530/788.22, 388.75, 389.6

[56] References Cited

U.S. PATENT DOCUMENTS

| | | |
|---|---|---|
| 4,544,632 | 10/1985 | Yamamura et al. . |
| 4,675,291 | 6/1987 | Yamamura et al. . |
| 4,839,290 | 6/1989 | Kaieda et al. . |
| 5,057,423 | 10/1991 | Hiserodt et al. . |
| 5,399,346 | 3/1995 | Anderson et al. . |

FOREIGN PATENT DOCUMENTS

| | | |
|---|---|---|
| 88/07077 | 9/1988 | WIPO . |
| 92/05794 | 4/1992 | WIPO . |
| 92/08796 | 5/1992 | WIPO . |

OTHER PUBLICATIONS

Sakai et al., "Dissociation of interleukin–2 production from the cell activation in response to the mitogenic lectin in peripheral CD4$^+$ T cells of LEC mutant rats" *Immunology* (1993) 79:491–497.

Sakai et al., "Expression of major histocompatibility complex class II but not of CD8 molecules by lectin–stimulated peripheral CD4$^+$ T cells in LEC mutant rats" *Cellular Immunology* (1994) 158:414–422.

Ciavarra et al., "Analysis of T–cell subset proliferation at afebrile and febrile temperatures: Differential response of Lyt–1$^+$23$^-$ lymphocytes to hyperthermia following mitogen and antigen stimulation and its functional consequence on development of cytotoxic lymphocytes" *Cellular Immunology* (1987) 107:293–306.

Heeg et al., "Clonal specificity analysis of mitogen–activated murine T lymphocytes" *Immunobiology* (1987) 175:446.

Miller et al., "Differential sensitivity of virgina and memory T lymphocytes to calcium ionophores suggests a buoyant density separation method and a model for memory cell hyporesponsiveness to con A$^{1}$" *Journal of Immunology* (1991) 147:3080–3086.

Lamb–Wharton et al., "Induction of T–lymphocyte adhesion by histidine–proline–rich glycoprotein and concanavalin A" *Cellular Immunology* (1993) 152:544–555.

Tiegs et al., "A T cell–dependent experimental liver injury in mice inducible by concanavalin A" *Journal of Clinical Investigation* (1992) 90:196–203.

Gantner et al., "Concanavalin A–induced T–cell–mediated hepatic injury in mice: The role of tumor necrosis factor" *Hepatology* (1995) 21:190–198.

Nagi et al., "Concanavalin A–induced suppressor cell activity in intestinal mucosal leukocytes obtained from healthy cows" *American Journal of Veterinary Research* (1989) 50:1266–1271.

Mazumder et al., "Phase I study of the adoptive immunotherapy of human cancer with lectin activated autologous Mononuclear cells" *Cancer* (1984) 53:896–905.

Van de Griend, et al., "Rapid expansion of human cytotoxic T cell clones; Growth promotion by Heat–labile serum component and by various types of feeder cells", *Journal of Immunological Methods* (1984), 66:285–298.

Van de Griend, et al., "Rapid expansion of allospecific cytotoxic T cell clones using non–specific feeder cell lines without further addition of exogenous IL2", *Transplantation* (1984), 38:401–406.

Weber et al., "Activation through CD3 molecule leads to clonal expansion of all human peripheral blood T lymphocytes: functional analysis of clonally expanded cells", *Journal of Immunology* (1985), 135: 2337–2342.

Greenberg, "Adoptive T cell therapy of tumors: Mechanisms operative in the recognition and elimination of tumor cells" *Adv. Immunol.* Dixon, F.J. ed., Academic Press, Inc., New York, (1991) 49:281–355.

(List continued on next page.)

*Primary Examiner*—Ronald B. Schwadron
*Attorney, Agent, or Firm*—Tyler M. Dylan; Morrison & Foerster LLP

[57] ABSTRACT

The present invention provides a rapid expansion method (termed "REM"), for quickly generating large numbers of T lymphocytes, including cytolytic and helper T lymphocytes. REM involves culturing the T cells in association with a disproportionately large concentration of nondividing feeder cells, preferably γ-irradiated peripheral blood mononuclear cells ("PBMC") present at an excess of at least 40-fold (relative to the number of target T cells), more preferably at an excess of at least about 200-fold. Cultures grown under REM exhibit dramatically enhanced expansion rates that can be even further elevated by the use of appropriate concentrations of an additional feeder cell, an anti-CD3 monoclonal antibody and IL-2, as described herein. Clonal expansions in the range of 500-fold to 3000-fold can be achieved within a single stimulation cycle of about 10–13 days, which is more than 100-fold more efficient than currently employed methods of culturing human T cell clones. Genetic transduction efficiencies were also enhanced using REM-expanded T lymphocytes. Several examples involving human bone marrow transplant recipients illustrate the effective use of REM-expanded antigen-specific cytotoxic T lymphocytes for adoptive immunotherapy in humans.

11 Claims, 15 Drawing Sheets

OTHER PUBLICATIONS

Riddell et al., "Restoration of viral immunity in immunodeficient humans by the adoptive transfer of T cell clones" *Science* (1992) 257:238–241.

Reusser et al., "Cytotoxic T–lymphocyte response to cytomegalovirus after human allogeneic bone marrrow transplantation: Pattern of recovery and correlation with cytomegalovirus infection and disease" *Blood* (1991) 78:1373–1380.

Riddell et al., "Class I MHC–restricted cytotoxic T lymphocyte recognition of cells infected with human cytomegalovirus does not require endogenous viral gene expression" *J. Immunol.* (1991) 146:2795–2804.

Ridell et al., "The use of anti–CD3 and anti–CD28 monoclonal antibodies to clone and expand human antigen–specific T cells" *J. Immunol. Meth.* (1990) 128:189–201.

Rosenberg et al., "A progress report on the treatment of 157 patients with advanced cancer using lymphokine–activated killer cells and interleukin–2 or high–dose interleukin–2 alone" *New Engl. J. Med.* (1987) 316:890–897.

Rosenberg et al., "Use of tumor–infiltrating lymphocytes and interleukin–2 in the immunotherapy of patients of metastatic melanoma" *New Engl. J. Med.* (1988) 319:1676–1680.

Ho et al., "A phase I study of adoptive transfer of autologous CD8$^+$ T lymphocytes in patients with acquired immunodeficiency syndrome (AIDS)–related complex or AIDS" *Blood* (1993) 81:2093–2101.

Gillis et al., "Interleukin–2 dependent culture of cytolytic T cell lines" *Immunol. Rev.* (1981) 54:81–109.

Paul et al., "Long–term growth and cloning of non–transformed lymphocytes" *Nature* (1981) 294:697–699.

Lenardo, "Interleukin–2 programs mouse $\alpha\beta$ T lymphocytes for apoptosis" *Nature* (1991) 353:858–861.

Boehme et al., "Propriocidal apoptosis of mature T lymphocytes occurs at S phase of the cell cycle" *Eur. J. Immunol.* (1993) 23:1552–1560.

Miller, "Retroviral vectors" *Current Topics in Microbiol. & Immunol.* (1992) 158:1–24.

Rosenberg et al., "Gene transfer into humans—immunotherapy of patients with advanced melanoma, using tumor–infiltrating lymphocytes modified by retroviral gene transduction" *New Engl. J. Med.* (1990) 323:570–578.

Springett et al., "Infection efficiency of T lymphocytes with amphotrophic retroviral vectors is cell cycle dependent" *J. Virol.* (1989) 63:3865–3869.

Roe et al., "Integration of murine leukemia virus DNA depends on mitosis" *EMBO J.* (1993) 12:2099–2108.

Burgess et al., "The nature and action of granulocyte–macrophage colony stimulating factors" *Blood* (1980) 56:947–958.

Crossland et al., "T cells from tumor–immune mice non-specifically expanded in vitro with anti–CD3 plus IL–2 retain specific function in vitro and can eradicate disseminated leukemia in vivp" *J. Immunol.* (1991) 146:4414–4420.

Gilbert et al., "Selective interference with class I major histocompatibility complex presentation of the major immediate–early protein following infection with human cytomegalovirus" *J. Virol.* (1993) 67:3461–3469.

Moore et al., "Culture of normal human leukocytes" *J. Am. Med. Assoc.* (1967) 199:87–92.

Riddell et al., "Phase I study of cellular adoptive immunotherapy using genetically modified CD8$^+$ HIV–specific T cells for HIV seropositive patients undergoing allogenic bone marrow transplant" *Human Gene Therapy* (1992) 3:319–338.

Schnook et al., "Lymphokine and monokine activities in supernatants from human lymphoid and myeloid cell lines" *Lymphokines* (1981) 2:1–19.

Weaver et al., "Syngeneic transplantation with peripheral blood mononuclear cells collected after the administraton of recombinant human granulocyte colony–stimulating factor" *Blood* (1993) 82:1981–1984.

| CLONE | PHENOTYPE | Ag SPECIFICITY | FLASK SIZE | INPUT CELL#/FLASK | CELL YIELD/ FLASK | FOLD EXPANSION |
|---|---|---|---|---|---|---|
| ER3C | CD3+CD8+CD4- | CMV | 25cm$^2$ | 5x10$^4$ | 5.6x10$^7$ | 1120 |
| ER12C | CD3+CD8+CD4- | CMV | 25cm$^2$ | 5x10$^4$ | 7.5x10$^7$ | 1500 |
| ER4G | CD3+CD8+CD4- | HIV | 25cm$^2$ | 5x10$^4$ | 4.7x10$^7$ | 940 |
| ER11G | CD3+CD8+CD4- | HIV | 25cm$^2$ | 5x10$^4$ | 5.9x10$^7$ | 1180 |
| DRG21A8 | CD3+CD8+CD4- | CMV | 25cm$^2$ | 6x10$^4$ | 5.2x10$^7$ | 866 |
| DRG9A4 | CD3+CD8+CD4- | CMV | 25cm$^2$ | 5x10$^4$ | 4.9x10$^7$ | 980 |
| DPN7B5 | CD3+CD8+CD4- | CMV | 25cm$^2$ | 5x10$^4$ | 7.1x10$^7$ | 1420 |
| DPN7F4 | CD3+CD8+CD4- | CMV | 25cm$^2$ | 5x10$^4$ | 6.4x10$^7$ | 1280 |
| DHTh-2 | CD3+CD4+CD8- | CMV | 25cm$^2$ | 5x10$^4$ | 5.4x10$^7$ | 1080 |
| DHTh-10 | CD3+CD4+CD8- | CMV | 25cm$^2$ | 5x10$^4$ | 6.1x10$^7$ | 1220 |
| MEAN | | | | | | 1159 |

FIG. 1

| CLONE | PHENOTYPE | Ag SPECIFICITY | FLASK SIZE/# | INPUT CELL#/FLASK | TOTAL CELL YIELD | FOLD EXPANSION |
|---|---|---|---|---|---|---|
| DRG28D3 | CD3+CD8+CD4- | CMV | 75cm²x20 | $2.25 \times 10^5$ | $8.0 \times 10^9$ | 1778 |
| DRG6C11 | CD3+CD8+CD4- | CMV | 75cm²x5 | $1.60 \times 10^5$ | $7.3 \times 10^8$ | 906 |
| MRL10E6 | CD3+CD8+CD4- | CMV | 75cm²x3 | $1.50 \times 10^5$ | $1.0 \times 10^9$ | 2231 |
| MRL10B5 | CD3+CD8+CD4- | CMV | 75cm²x12 | $1.50 \times 10^5$ | $3.5 \times 10^9$ | 1944 |
| DRD23C9 | CD3+CD8+CD4- | CMV | 75cm²x10 | $1.50 \times 10^5$ | $1.2 \times 10^9$ | 800 |
| LAH7E4 | CD3+CD8+CD4- | CMV | 75cm²x20 | $3.0 \times 10^5$ | $9.0 \times 10^9$ | 1500 |
| LAH4F8 | CD3+CD8+CD4- | CMV | 75cm²x10 | $3.0 \times 10^5$ | $3.0 \times 10^9$ | 1000 |
| RM56G6/9 | CD3+CD8+CD4- | HIV | 75cm²x5 | $5.0 \times 10^5$ | $6.2 \times 10^9$ | 248 |
| RM56G6/2 | CD3+CD8+CD4- | HIV | 75cm²x5 | $5.0 \times 10^5$ | $1.5 \times 10^9$ | 600 |
| JTE10A5/5 | CD3+CD8+CD4- | HIV | 75cm²x45 | $4.1 \times 10^5$ | $6.0 \times 10^9$ | 326 |
| MEAN | | | | | | 1133 |

FIG. 2

| CLONE | PHENOTYPE | Ag SPECIFICITY | FOLD INCREASE (a) REM | FOLD INCREASE (b) αCD3 | FOLD INCREASE (c) Ag |
|---|---|---|---|---|---|
| ER10C | CD3+CD8+CD4- | CMV | 550 | 16 | 1.8 |
| ER12C | CD3+CD8+CD4- | CMV | 1500 | 21 | 1.5 |
| ER4G | CD3+CD8+CD4- | HIV | 940 | 25 | N.D. |
| ER11G | CD3+CD8+CD4- | HIV | 1180 | 6 | N.D. |
| LAH4F8 | CD3+CD8+CD4- | CMV | 1560 | 4 | 2.2 |
| LAH7E4 | CD3+CD8+CD4- | CMV | 2970 | 10 | 6.4 |
| MEAN | | | 1450 | 14 | 3 |

FIG. 5

% LYSIS

| CLONE | E/T | AUTOLOGOUS TARGET CELLS | | | HLA MISMATCHED TARGET CELLS | | |
|---|---|---|---|---|---|---|---|
| | | VAC/gag | VAC | MOCK | VAC/gag | VAC | MOCK |
| RM56G6/9 | 5:1 | 55 | 0 | 4 | 2 | 1 | 1 |
| | 2:1 | 64 | 0 | 5 | 0 | 1 | 1 |
| | 1:1 | 60 | 0 | 5 | 1 | 2 | 1 |
| RM56G6/2 | 5:1 | 53 | 2 | 1 | 2 | 2 | 2 |
| | 2:1 | 53 | 2 | 1 | 1 | 1 | 2 |
| | 1:1 | 42 | 1 | 1 | 1 | 2 | 1 |
| JTE10A5/5 | 10:1 | 78 | 0 | 2 | 0 | 1 | N.D. |
| | 5:1 | 72 | 1 | 1 | 0 | 1 | N.D. |
| JTE10A5/13 | 10:1 | 79 | 0 | 1 | 2 | 1 | N.D. |
| | 10:1 | 75 | 0 | 3 | 2 | 1 | N.D. |

FIG. 8

% LYSIS

| CLONE | E/T | AUTOLOGOUS CELLS | | HLA MISMATCHED TARGET CELLS | |
|---|---|---|---|---|---|
| | | CMV | MOCK | CMV | MOCK |
| LAH4F8 | 10:1 | 30 | 0 | 0 | 0 |
| | 5:1 | 29 | 0 | 0 | 0 |
| LAH7E4 | 10:1 | 41 | 0 | 0 | 0 |
| | 5:1 | 32 | 0 | 0 | 0 |
| MRL10E6 | 10:1 | 47 | 0 | 1 | 1 |
| | 5:1 | 42 | 0 | 0 | 0 |
| MRL10B5 | 10:1 | 59 | 0 | 2 | 1 |
| | 5:1 | 44 | 0 | 0 | 0 |

FIG. 9

RAPID EXPANSION METHOD ("REM") FOR IN VITRO PROPAGATION OF T LYMPHOCYTES

CROSS-REFERENCE TO RELATED APPLICATION

This application is a continuation of U.S. patent application Ser. No. 08/299,930, filed Aug. 31, 1994 now abandoned; incorporated herein by reference.

This invention was funded in part by National Institutes of Health Grant No. CA-18029. The United States Government may have certain rights in the invention.

FIELD OF THE INVENTION

This invention relates to improved methods for culturing T lymphocytes, including human antigen-specific cytolytic and helper T lymphocytes. The method of the present invention results in the very rapid and efficient expansion of T cells which are useful, for example, in adoptive immunotherapy.

BACKGROUND

T lymphocytes are formed in the bone marrow, migrate to and mature in the thymus and then enter the peripheral blood and lymphatic circulation. T lymphocytes are subdivided into three distinct types of cells: helper T cells, suppressor T cells, and cytotoxic T cells. T lymphocytes, unlike B lymphocytes, do not produce antibody molecules, but express a heterodimeric cell surface receptor that recognizes peptide fragments of antigenic proteins that are attached to proteins of the major histocompatibility complex (MHC) and expressed on the surfaces of target cells; see, e.g., Abbas, A. K., Lichtman, A. H., and Pober, J. S., *Cellular and Molecular Immunology*, 1991, esp. pages 15–16.

Cytotoxic T lymphocytes (CTLs) are typically of the CD3+, CD8+, CD4– phenotype and lyse cells that display fragments of foreign antigens associated with class I MHC molecules on their cell surfaces. Target cells for CTL recognition include normal cells expressing antigens after infection by viruses or other pathogens; and tumor cells that have undergone transformation and are expressing mutated proteins or are over-expressing normal proteins.

Helper T cells are also CD3+ but can be distinguished from cytolytic T cells by expression of CD4 and absence of the CD8 membrane protein. CD4+ helper T cells recognize fragments of antigens presented in association with class II MHC molecules, and primarily function to produce cytokines that amplify antigen-specific T and B cell responses and activate accessory immune cells such as monocytes or macrophages. See, e.g., Abbas, A. K., et al., supra.

CD4+ helper and CD8+ cytotoxic T lymphocytes are important components of the host immune response to viruses, bacterial pathogens and tumors. As a result, individuals with congenital, acquired or iatrogenic T cell immunodeficiency diseases may develop life threatening infections or malignancies (for example, SCID, BMT, AIDS, etc.). Persons with diseases that are related to a deficiency of immunologically competent T lymphocytes can potentially have specific immunity restored through adoptive immunotherapy, alternatively called adoptive transfer. In adoptive immunotherapy, one or more specific immunities can be conferred upon an individual by transferring T cells having the desired antigenic specificities. The cells of interest may be derived from the immunodeficient host or from a compatible specifically immunized host. The latter source is of course especially important in situations in which the immunodeficient host has an insufficient number of T cells, or has T cells that are insufficiently effective.

In order to augment or reconstitute T cell responses in such immunodeficient hosts, the antigen-specific T cells must be grown to large numbers in vitro and then administered intravenously to the immune-deficient host. After undergoing adoptive immunotherapy, hosts that previously had inadequate or absent responses to antigens expressed by pathogens or tumors, may express sufficient immune responses to become resistant or immune to the pathogen or tumor.

Adoptive transfer of antigen-specific T cells to establish immunity has been demonstrated to be an effective therapy for viral infections and tumors in animal models (reviewed in Greenberg, P. D., *Advances in Immunology* (1992)). For adoptive immunotherapy to be effective, antigen-specific T cells usually need to be isolated and expanded in numbers by in vitro culture, and following adoptive transfer such cultured T cells must persist and function in vivo. For treatment of human disease, the use in immunotherapy of cloned antigen-specific T cells which represent the progeny of single cells, offers significant advantages because the specificity and function of these cells can be rigorously defined and precise dose:response effects evaluated. Riddell et al. were the first to adoptively transfer human antigen-specific T cell clones to restore deficient immunity in humans. Riddell, S. R. et al., "Restoration of Viral Immunity in Immunodeficient Humans by the Adoptive Transfer of T Cell Clones", *Science* 257:238–240 (1992). In this study, Riddell et al. used adoptive immunotherapy to restore deficient immunity to cytomegalovirus in allogeneic bone marrow transplant recipients. Cytomegalovirus specific CD8+ cytotoxic T cell clones were isolated from three CMV seropositive bone marrow donors, propagated in vitro for 5 to 12 weeks to achieve numerical expansion of effector T cells, and then administered intravenously to the respective bone marrow transplant (BMT) recipients. The BMT recipients were deficient in CMV-specific immunity due to ablation of host T cell responses by the pretransplant chemoradiotherapy and the delay in recovery of donor immunity commonly observed after allogeneic bone marrow transplant (Reusser et al. *Blood*, 78:1373–1380, 1991). Riddell et al. found that no toxicity was encountered and that the transferred T cell clones provided these immunodeficient hosts with rapid and persistent reconstitution of CD8+ cytomegalovirus-specific CTL responses.

Riddell et al. (*J. Immunology*, 146:2795–2804, 1991) used the following procedure for isolating and culturing the CD8+ CMV-specific T cell clones: peripheral blood mononuclear cells (PBMCs) derived from the bone marrow donor were first cultured with autologous cytomegalovirus-infected fibroblasts to activate CMV-specific CTL precursors. Cultured T cells were then restimulated with CMV-infected fibroblasts and the cultures supplemented with γ-irradiated PBMCs. 2–5 U/ml of interleukin-2 (IL-2) in suitable culture media was added on days 2 and 4 after restimulation to promote expansion of CD8+ CTL (Riddell et al., *J. Immunol.*, 146:2795–2804, 1991). To isolate T cell clones, the polyclonal CD8+ CMV-specific T cells were plated at limiting dilution (0.3–0.6 cells/well) in 96-well round bottom wells with either CMV-infected fibroblasts as antigen-presenting cells (Riddell, *J. Immunol.*, 146:2795–2804, 1991); or αCD3 monoclonal antibody to mimic the stimulus provided by antigen-presenting cells. (Riddell, *J. Imm. Methods*, 128:189–201, 1990). Then, γ-irradiated peripheral blood mononuclear cells (PBMC)

and EBV-transformed lymphoblastoid cell line (LCL) were added to the microwells as feeder cells. Wells positive for clonal T cell growth were evident in 10–14 days. The clonally derived cells were then propagated to large numbers initially in 48 or 24 inch plates and subsequently in 12-well plates or 75-cm$^2$ tissue culture flasks. T cell growth was promoted by restimulation every 7–10 days with autologous CMV-infected fibroblasts and γ-irradiated feeder cells consisting of PBMC and LCL, and the addition of 25–50 U/ml of IL-2 at 2 and 4 days after restimulation.

A major problem that exists in the studies described above, and in general in the prior art of culturing T cells, is the inability to grow large quantities of human antigen-specific T cell clones in a timely fashion. It is not known if the slow growth of T cells in culture represents an inherent property of the cell cycle time for human lymphocytes or the culture conditions used. For example, with the culture method used in the CMV adoptive immunotherapy study described above, three months were required to grow T cells to achieve the highest cell dose under study which was $1 \times 10^9$ T cells/cm$^2$. This greatly limits the application of adoptive immunotherapy for human viral diseases and cancer since the disease process may progress during the long interval required to isolate and grow the specific T cells to be used in therapy. Based on extrapolation from animal model studies (reviewed in Greenberg, P. D., Advances in Immunology, 1992), it is predicted that in humans doses of antigen-specific T cells in the range of $10^9$–$10^{10}$ cells may be required to augment immune responses for therapeutic benefit. However, rapidly expanding antigen-specific human T cells in culture to these cell numbers has proven to be a significant obstacle. Thus, with the exception of the study by Riddell et al., supra, studies of adoptive immunotherapy using antigen-specific T cell clones have not been performed. The problem of producing large numbers of cells for adoptive immunotherapy was identified in U.S. Pat. No. 5,057,423. In this patent, a method for isolating pure large granular lymphocytes and a method for the expansion and conversion of these large granular lymphocytes into lymphokine activated killer (LAK) cells is described. The methods are described as providing high levels of expansion, i.e up to 100-fold in 3–4 days of culture. Although LAK cells will lyse some types of tumor cells, they do not share with MHC-restricted T cells the properties of recognizing defined antigens and they do not provide immunologic memory. Moreover, the methods used to expand LAK cells, which predominantly rely on high concentrations of IL-2 do not efficiently expand antigen-specific human T cells (Riddell et al., unpublished); and those methods can render T cells subject to programmed cell death (i.e. apoptosis) upon withdrawal of IL-2 or subsequent stimulation via the T cell receptor (see the discussion of the papers by Lenardo et al, and Boehme et al., infra).

The inability to culture antigen-specific T cell clones to large numbers has in part been responsible for limiting adoptive immunotherapy studies for human diseases such as cancer (Rosenberg, *New Engl. J. Med.,* 316:1310–1321, 1986; Rosenberg, *New Engl. J. Med.,* 319:1676–1680, 1988) and HIV infection (Ho M. et al., *Blood* 81:2093–2101, 1993) to the evaluation of activated polyclonal lymphocyte populations with poorly defined antigen specificities. In such studies, polyclonal populations of lymphocytes are either isolated from the blood or the tumor filtrate and cultured in high concentrations of the T cell growth factor IL-2. In general, these cells have exhibited little if any MHC-restricted specificity for the pathogen or tumor and in the minority of patients that have experienced therapeutic benefit, it has been difficult to discern the effector mechanism involved. Typically, adoptive immunotherapy studies with non-specific effector lymphocytes have administered approximately $2 \times 10^{10}$ to $2 \times 10^{11}$ cells to the patient. (See, e.g., U.S. Pat. No. 5,057,423, at column 1, lines 40–43).

The development of efficient cell culture methods to rapidly grow T lymphocytes will be useful in both diagnostic and therapeutic applications. In diagnostic applications, the ability to rapidly expand T cells from a patient can be used, for example, to quickly generate sufficient numbers of cells for use in tests to monitor the specificity, activity, or other attributes of a patient's T lymphocytes. Moreover, the capability of rapidly achieving cell doses of $10^9$–$10^{10}$ cells will greatly facilitate the applicability of specific adoptive immunotherapy for the treatment of human diseases.

There are several established methods already described for culturing cells for possible therapeutic use including methods to isolate and expand T cell clones. Typical cell culture methods for anchorage dependent cells, (i.e., those cells that require attachment to a substrate for cell proliferation) are limited by the amount of surface area available in culture vessels used (i.e., multi-well plates, petri dishes, and culture flasks). For anchorage dependent cells, the only way to increase the number of cells grown is to use larger vessels with increased surface area and/or use more vessels. However, hemopoietic derived cells such as T lymphocytes are anchorage independent. They can survive and proliferate in response to the appropriate growth factors in a suspension culture without attachment to a substrate. Even with the ability to grow antigen-specific lymphocytes in a suspension culture, the methods reported to date have not consistently produced rapid numerical expansion of T cell clones. For example, in a study of T cells conducted by Gillis and Watson, it was found that T cells cultured at low densities, i.e., $5 \times 10^3$ to $1 \times 10^4$ cell/ml in the presence of the T cell growth factor IL-2, proliferated rapidly over a seven day period and eventually reached a saturation density of $3$–$5 \times 10^5$ cells/ml. Gillis, S. and Watson, J. "Interleukin-2 Dependent Culture of Cytolytic T Cell Lines", *Immunological Rev.,* 54:81–109 (1981). Furthermore, Gillis and Watson also found that once cells reached this saturation concentration, the cells would invariably die. Gillis et al., id.

Another study reports three different methods for establishing murine T lymphocytes in long-term culture. Paul et al., report that the method most widely used is to grow T lymphocytes from immunized donors for several weeks or more in the presence of antigen and antigen presenting cells to provide the requisite T cell receptor signal and costimulatory signals, and with the addition of exogenous growth factors before attempting to clone them, Paul, W. E., et al., "Long-term growth and cloning of non-transformed lymphocytes", *Nature,* 294:697–699, (1981). T cells specific for protein antigens are then cloned by limiting dilution with antigen and irradiated spleen cells as a source of antigen-presenting cells (APCs). A second method involves growing T cells as colonies in soft agar as soon as possible after taking the cells from an immunized donor. The T cells are stimulated in an initial suspension culture with antigen and a source of APCs, usually irradiated spleen cells. In this second approach, it has been found that, after 3 days, the cells are distributed in the upper layer of a two-layer soft agar culture system. The colonies may be picked from day 4 to 8 and then expanded in long-term cultures. The third approach involves selecting cells for their functional properties rather than their antigenic specificity and then growing them with a series of different irradiated feeder cells and growth factor containing supernatants. Paul, W. E. et al., "Long-term growth and cloning of non-transformed lymphocytes", Nature, 294:697–699, (1981). It is apparent that with each of these methods, it is not possible to expand individual T cell clones from a single cell to $10^9$–$10^{10}$ cells in a timely manner. Thus, despite the ability to clone antigen-specific T cells, and convincing evidence of the therapeutic efficacy of T cell clones in accepted animal models, the technical difficulty in culturing human T cells to large numbers has impeded the clinical evaluation of specific adoptive immunotherapy.

Yet another concern with cultured T cells is that they must remain capable of functioning in vivo in order to be useful in adoptive immunotherapy. In particular, it has been observed that antigen-specific T cells which were grown long term in culture in high concentrations of IL-2 may develop cell cycle abnormalities and lose the ability to return to a quiescent phase when IL-2 is withdrawn. In contrast, the normal cell cycle consists of four successive phases: mitosis (or "M" phase) and three phases which make up the "interphase" stage. During the M phase, the cell undergoes nuclear division and cytokinesis, which is cytoplasmic division. The interphase stage consists of the $G_1$ phase in which the biosynthetic activities resume at a high rate after mitosis; the S phase in which DNA synthesis begins and continues until the DNA content of the nucleus has doubled and the chromosomes are replicated; and the $G_2$ phase which continues until mitosis commences. While in the $G_1$ phase, some cells appear to cease progressing through the division cycle; and are said to be in a "resting" or quiescent state denoted as the "$G_0$" state. Certain environmental factors (such as a lack of growth factors in serum or confluence of cell cultures) may cause cells to enter the quiescent state. Once the factor is restored, the cell should resume its normal progress through the cycle. However, cells grown in culture may be unable to enter the quiescent phase when the growth factor is removed, resulting in the death of these cells. This growth factor dependence is particularly relevant to cultured T cells. T lymphocytes that are exposed to high concentrations of IL-2 to promote cell growth often will die by a process called apoptosis if IL-2 is removed or if they are subsequently stimulated through the T cell receptor, i.e., if they encounter specific antigens. (Lenardo M. J., Nature, 353:858–861, 1991; Boehme S. A. and Lenardo M. J., Eur. J. Immunol., 23:1552–1560, 1992). Therefore, the culture methods used to propagate LAK cells or TIL-cells and prior methods to culture T cells which predominantly rely on high concentrations of IL-2 to promote expansion in vitro may render many of the cells susceptible to apoptosis, thus limiting or eliminating their usefulness for adoptive transfer.

It may also be advantageous in adoptive immunotherapy studies to use gene transfer methods to insert foreign DNA into the T cells to provide a genetic marker, which facilitates evaluation of in vivo migration and survival of transferred cells or to confer functions that may improve the safety and efficacy of transferred T cells. An established method for stable gene transfer into mammalian cells is the use of amphotropic retroviral vectors (Miller A D, Current Tonics in Microbiology and Immunology, 158:1–24, 1992). The stable integration of genes into the target cell with retrovirus vectors requires that the cell be actively cycling, specifically that these cells transit M phase of the cell cycle. Prior studies have introduced a marker gene into a small proportion of polyclonal T cells driven to proliferate with high doses of IL-2 and these cells were reinfused into humans as tumor therapy and provided a means of following the in vivo survival of transferred cells. (Rosenberg et al. New Engl. J. Med., 323:570–578, 1990). However, for human T cells (which cycle slowly when grown with standard techniques) the efficiency of stable gene transfer is very low, in the range of 0.1–1% of T cells. (Springett C M et al. J. Virology, 63:3865–69, 1989). Culture methods which more efficiently recruit the target T cells into the S and G2-M phases of the cell cycle may increase the efficiency of gene modification using retrovirus-mediated gene transfer (Roe T. et al., EMBO J, 2:2099–2108, 1993), thus improving the prospects for using genetically modified T cells in adoptive immunotherapy or using T cells to deliver defective genes in genetic deficiency diseases.

BRIEF SUMMARY OF THE INVENTION

This invention provides a method for rapidly producing large numbers of T cells, including human antigen-specific cytolytic and helper T cells, isolated from an initial population of T cells. While the methods of the present invention are applicable to the rapid expansion of T lymphocytes, generally, the rapid expansion method will be especially advantageous in situations in which an individual T cell clone must be expanded to provide a large population of T lymphocytes. Thus, the present invention provides an especially important tool in the context of human adoptive immunotherapy, as has been exemplified in studies (described below) involving human bone marrow transplant recipients at the Fred Hutchinson Cancer Research Center. The present invention also provides a method to improve the efficiency of stable gene transfer into T lymphocytes, as exemplified below.

Accordingly, one object of the invention is to rapidly expand T lymphocytes to large numbers in vitro. Such rapidly expanded T cell populations can be used, inter alia, for infusion into individuals for the purpose of conferring a specific immune response, as exemplified herein. The T cells can be either CD8+ cytotoxic T cells or CD4+ helper T cells, and they can react with antigens encoded in any of a variety of virally infected cells or tumor cells.

Another object of the invention is to use the method to grow T cells in a manner which facilitates the stable introduction of foreign genetic material which could be used to alter the function of T cells to be used in adoptive immunotherapy or to replace a defective gene in the host.

A number of preferred embodiments of the present invention are described in the following enumeration:

1. A method for rapidly expanding an initial T lymphocyte population in culture medium in vitro, comprising the steps of:

adding an initial T lymphocyte population to a culture medium in vitro;

adding to the culture medium a disproportionately large number of non-dividing peripheral blood mononuclear cells (PBMC) as feeder cells such that the resulting population of cells contains at least about 40 PBMC feeder cells for each T lymphocyte in the initial population to be expanded; and incubating the culture.

The culture will be incubated under conditions of temperature and the like that are suitable for the growth of T lymphocytes. For the growth of human T lymphocytes, for example, the temperature will generally be at least about 25 degrees celsius, preferably at least about 30 degrees, more preferably about 37 degrees. Descriptions of suitable media and other culture conditions are well-known in the art, and are also exemplified herein.

2. The rapid expansion method of item 1, wherein the initial T lymphocyte population comprises at least one human CD8+ antigen-specific cytotoxic T lymphocyte (CTL). In preferred embodiments of the present invention, the CTL is specific for an antigen present on a human tumor or a pathogen.

3. The rapid expansion method of item 1, wherein the initial T lymphocyte population comprises at least one human CD4+ antigen-specific helper T lymphocyte.

4. The rapid expansion method of item 1, wherein the non-dividing feeder cells comprise gamma-irradiated PBMC feeder cells. Preferably, PBMC are irradiated with gamma rays in the range of about 3000 to 3600 rads, more preferably at about 3300 rads.

5. The rapid expansion method of item 1, wherein the ratio of PBMC feeder cells to initial T lymphocytes is at least about 200:1.

6. The rapid expansion method of item 5, wherein the ratio of PBMC feeder cells to initial T lymphocytes is between about 400:1 and 800:1. Typically, we use a ratio of about 500:1.

7. The rapid expansion method of item 1, further comprising the step of adding non-dividing EBV-transformed lymphoblastoid cells (LCL) as feeder cells. Preferably, LCL are irradiated with gamma rays in the range of about 6000 to 10,000 rads, more preferably at about 8000 rads.

8. The rapid expansion method of item 7, wherein the ratio of LCL feeder cells to initial T lymphocytes is at least about 10:1.

9. The rapid expansion method of item 8, wherein the ratio of LCL feeder cells to initial T lymphocytes is between about 50:1 and 200:1. Typically, we use a ratio of about 100:1.

10. The rapid expansion method of item 1, further comprising the step of adding anti-CD3 monoclonal antibody to the culture medium.

11. The rapid expansion method of item 10, wherein the concentration of anti-CD3 monoclonal antibody is at least about 0.5 ng/ml.

12. The rapid expansion method of item 11, wherein the concentration of anti-CD3 monoclonal antibody is at least about 1.0 ng/ml. Typically, we use a concentration of about 30 ng/ml although much lower levels can be used, as illustrated below.

13. The rapid expansion method of item 1, further comprising the step of adding IL-2 to the culture medium.

14. The rapid expansion method of item 13, wherein the concentration of IL-2 is at least about 10 units/ml. Typically, we use a concentration of about 30 units/ml.

15. The rapid expansion method of item 14, wherein the incubation is continued for at least about 9 days and wherein the step of adding IL-2 to the culture medium is repeated after each 3–5 day interval. Typically, we add IL-2 on day 1, again on day 5 or 6, and again on day 8 or 9.

16. A method of genetically transducing a human T cell, comprising the steps of: adding an initial T lymphocyte population to a culture medium in vitro; adding to the culture medium a disproportionately large number of nondividing peripheral blood mononuclear cells (PBMC) as feeder cells such that the resulting population of cells contains at least about 40 PBMC feeder cells for each T lymphocyte in the initial population to be expanded; incubating the culture; and adding a vector to the culture medium. A vector refers to a unit of DNA or RNA in a form which is capable of being introduced into a target cell. Transduction is used generally to refer to the introduction of such exogenous DNA or RNA into a target cell and includes the introduction of heterologous DNA or RNA sequences into target cells by, e.g., viral infection and electroporation. A currently preferred method of transducing T lymphocytes is to use retroviral vectors, as exemplified herein.

17. The genetic transduction method of claim 16, further comprising adding non-dividing EBV-transformed lymphoblastoid cells (LCL) as additional feeder cells.

18. The genetic transduction method of item 17, wherein the vector is a retroviral vector containing a selectable marker providing resistance to an inhibitory compound that inhibits T lymphocytes, and wherein the method further comprises the steps of: continuing incubation of the culture for at least one day after addition of the retroviral vector; and adding said inhibitory compound to the culture medium after said continued incubation step.

19. The genetic transduction method of item 18, wherein the retroviral vector contains both a positive and a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

20. The genetic transduction method of item 19, wherein the retroviral vector encodes as a fusion gene the hygromycin phosphotransferase gene and the Herpes simplex virus thymidine kinase gene.

BRIEF DESCRIPTION OF THE DRAWINGS

FIG. 1 is an illustration of the rapid expansion of human antigen-specific cytotoxic T lymphocyte clones and antigen-specific helper T lymphocyte clones from 4 human donors, as described in Example 1.

FIG. 2 is an illustration of the large-scale expansion of antigen-specific T cell clones from 6 human donors for use in adoptive immunotherapy, as described in Example 2.

FIG. 5 is an illustration of the comparison of the rapid expansion method with other methods used for the propagation of T cells, as described in Example 5.

FIG. 8 is an illustration of data showing that HIV-specific CD8+ cytotoxic T lymphocytes retain antigen-specific lytic functions after rapid expansion, as described in Example 8.

FIG. 9 is an illustration of data showing that CMV-specific CD8+ cytotoxic T lymphocytes retain antigen-specific lytic functions after rapid expansion, as described in Example 9.

DETAILED DESCRIPTION OF THE INVENTION

Figure 3:
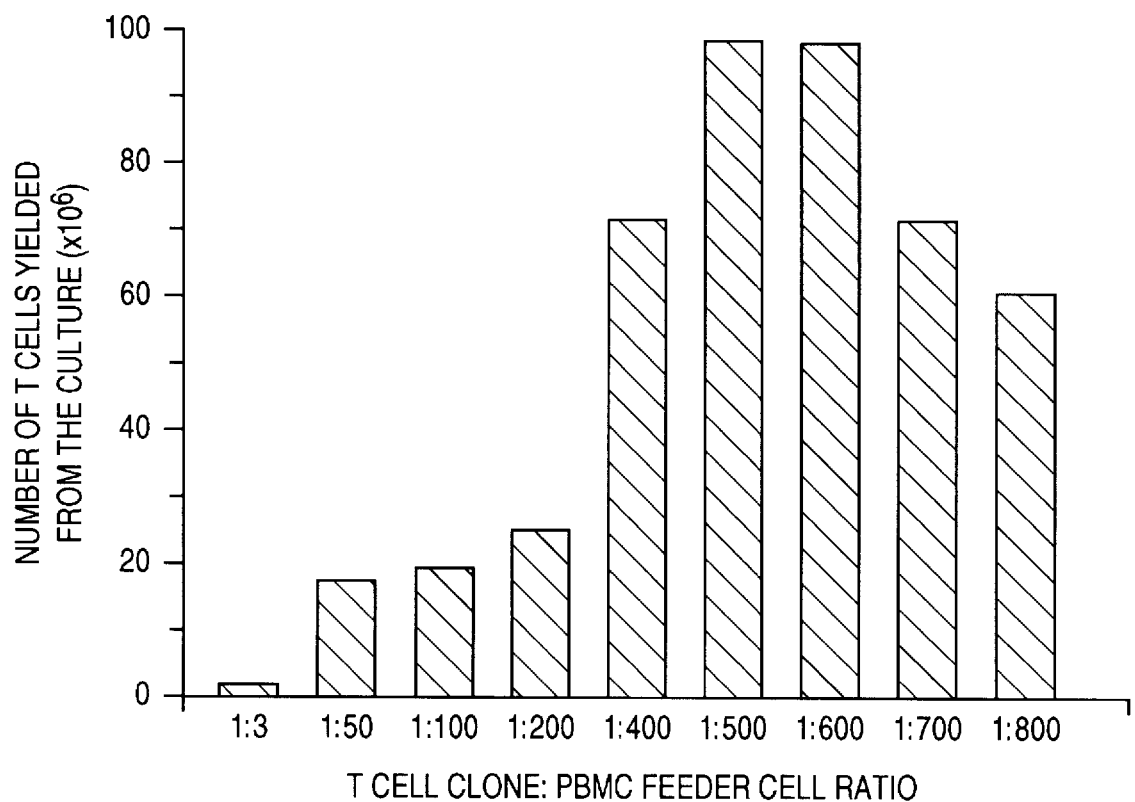
FIG. 3 is an illustration of the effect of the ratio of PBMC feeder cells to T cells in the rapid expansion method, as described in Example 3.

The invention described herein provides methods for rapidly expanding populations of T lymphocytes, including human cytotoxic T lymphocytes and helper T lymphocytes, which can be particularly useful in adoptive immunotherapy of human diseases.

The T cells will be referred to as "target T cells". In general, target T cells are added in small numbers to a culture vessel and standard growth medium that has been supplemented with: (i) an appropriate amount of antibody directed at the CD3 component of the T cell receptor complex to provide the T cell receptor signal; and (ii) a disproportionately large number of feeder cells, preferably gamma-irradiated PBMC as described below, which provide co-stimulatory signals. Preferably, human recombinant IL-2 or another suitable IL-2 preparation is added in low concentrations at 3–5 day intervals (typically on day 1, on day 5 or 6, and on day 8 or 9). The method of the present invention results in a rapid expansion of T cells, typically in the range of a 500- to 3000-fold expansion in 8 to 14 days. The present method is thus approximately 100- to 1000-fold more efficient for each stimulation cycle than currently described methods of culturing human T cells.

Furthermore, these methods are applicable to the rapid expansion of both helper T cells and cytolytic T cell populations; and to T cell clones of many different antigenic specificities (e.g., to cytolytic or helper T cells specific for CMV, HIV, or other viral or tumor-derived antigens). In addition, the methods of the present invention can be used for both small scale growth (e.g. to rapidly expand T cells from $10^4$ to $10^7$ cells); or for large scale expansions (e.g. to rapidly expand T cells from $10^6$ to greater than $10^{10}$ cells); depending on the size of culture vessel chosen.

The present invention thus makes it possible to efficiently expand T cell clones for use in adoptive immunotherapy, by dramatically shortening the time required to grow the numbers of cells required to modulate human immunity. For example, in the study by Riddell et al. (*Science,* 257:238–240, 1992), once T cell clones were isolated it was necessary to culture the clones for twelve weeks and to pool multiple clones to achieve the highest administered cell dose of $1 \times 10^9$ CD8+ CMV-specific T cells/m$^2$ body surface area. Using the methods of the present invention, the expansion of individual T cell clones to greater than $10^9$ cells can be accomplished in less than three weeks.

The practice of the present invention will employ, unless otherwise indicated, conventional techniques of molecular biology, microbiology, cell biology, recombinant DNA, and immunology, which are within the skill of the art. Such techniques are explained fully in the literature. See e.g., Sambrook, Fritsch, and Maniatis, *Molecular Cloning: A Laboratory Manual,* Second Edition (1989), *Oligonucleotide Synthesis* (M. J. Gait Ed., 1984), *Animal Cell Culture* (R. I. Freshney, Ed., 1987), the series *Methods in Enzymology* (Academic Press, Inc.); *Gene Transfer Vectors for Mammalian Cells* (J. M. Miller and M. P. Calos eds. 1987), *Handbook of Experimental Immunology,* (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

As an aid in understanding this invention, the following is a list of some abbreviations commonly used herein:

CTL cytotoxic T lymphocytes
APC antigen-presenting cells
CMV cytomegalovirus
HIV human immunodeficiency virus
EBV Epstein Barr virus
hIL-2 human interleukin-2
MHC major histocompatibility complex
PBMC peripheral blood mononuclear cells
LCL EBV transformed lymphoblastoid cell line
PBS phosphate buffered solution The T cells to be propagated in culture (i.e., the target T-cells) can be obtained from the subject to be treated. Alternatively, T cells can be obtained from persons other than the subject to be treated provided that the recipient and transferred cells are immunologically compatible. Typically, the cells are derived from tissue, bone marrow, fetal tissue, or peripheral blood. Preferably, the cells are derived from peripheral blood. If the T cells are derived from tissues, single cell suspensions should be prepared using a suitable medium or diluent. The generation of polyclonal populations of T cells is illustrated in the Examples below, see, esp., Example 12.

Mononuclear cells containing the T lymphocytes are isolated from the heterogenous population according to any of the methods well known in the art. As illustrative examples, Ficoll-Hypaque gradient centrifugation, fluorescence-activated cell sorting (FACs), panning on monoclonal antibody coated plates, and/or magnetic separation techniques can be used (separately or in combination) to obtain purified populations of cells for expansion according to the present invention. Antigen-specific T cell clones are isolated by standard culture techniques known in the art involving initial activation of antigen-specific T cell precursors by stimulation with antigen-presenting cells and subsequent cloning by limiting dilution cultures using techniques known in the art, such as those described in Riddell and Greenberg (*J. Immunol. Meth.,* 128:189–201, 1990); and Riddell et al. (*J. Immunol.,* 146:2795–2804, 1991). See also, the Examples below.

The T cell clones isolated in microwells in limiting dilution cultures typically have expanded from a single cell to $2 \times 10^4$ to $5 \times 10^5$ cells after 14 days. At this time individual clones are placed in appropriate culture media in plastic culture vessels with disproportionately large numbers of feeder cells which provide co-stimulatory functions, and, preferably, anti-CD3 monoclonal antibody to provide T cell receptor stimulation. This initial phase of rapid expansion when the clone is transferred from a microwell is generally carried out in a culture vessel, the size of which depends upon the number of target cells, and which may typically be a 25 cm$^2$ flask. The size of the culture vessel used for subsequent cycles of T cell expansion depends on the starting number of T cells and the number of cells needed (usually for therapeutic use). Typical starting cell numbers for different sized culture vessels are as follows: 5×10$^4$ to 2×10$^5$—approximately 25cm$^2$ flask; 2×10$^5$ to 5×10$^5$—approximately 75 cm flask; 5×10$^5$ to 1×10$^6$—approximately 225-cm$^2$ flask; and 1×10$^6$ to 2×10$^6$—roller bottle. The approximate initial volume of media used with each flask is: 25 cm$^2$—20–30 ml; 75 cm$^2$—60–90 ml; 225 cm$^2$—100–200 ml; roller bottle—500 ml.

As illustrated below, studies using 10 different T cell clones of varying antigen specificities, that were initially derived from 4 different human donors, indicate that a 500- to 3000-fold expansion in clonal T cell number (mean, 1200-fold) can be readily achieved within a single 10–13 day cycle of growth using the rapid expansion method of the present invention (see Example 1).

As illustrated in Example 2, the rapid expansion method can be readily scaled up to produce large numbers of antigen-specific T cells (greater than 10$^9$ cells) for use in adoptive immunotherapy. In that example, large numbers of CMV-specific and HIV-specific T cells were generated from 10 clones initially derived from 6 different human donors.

As used herein, "feeder cells" are accessory cells (such as the preferred γ-irradiated PBMC and LCL cells) that provide co-stimulating functions in conjunction with T cell receptor activation (which can be achieved by ligation of the T cell receptor complex with anti-CD3 monoclonal antibody). One aspect of the methods of the present invention that differs dramatically from prior methods of culturing human T cells is the disproportionately large ratio of the number of feeder cells used relative to the number of target T cells. As illustrated below in Example 3, for optimal growth of the T cells, the ratio of T cells:PBMC should be at least about 1:40 (i.e. at least about a 40-fold excess of PBMC), preferably the T cell:PBMC ratio is at least about 1:200, more preferably it is between about 1:400 and 1:800. Typically, we use a ratio of about 1:500.

As illustrated below in Example 4, the expansion can be even further enhanced by the inclusion of LCL feeder cells, preferably at a T cell:LCL ratio of at least about 1:10, more preferably at least about 1:20, still more preferably between about 1:50 and 1:200, most preferably about 1:100.

Typically in the past, it was common to coat anti-CD3 mAb onto a plate and to use no feeder cells in cultures to grow T cells; or, if feeder cells were employed, they were used at very much lower ratios of feeder cells to T cells (e.g. 1:1 to 10:1); see, e.g., Garbrecht F. C. et al. *J. Immunol. Methods* 107:137–142, 1980; Riddell, *J. Immunol. Meth.* 128:189–201, 1990; and Londei M., et al., *Scand J. Immunol.* 27:35–46, 1988. As illustrated in Example 5, below, direct comparisons of T cells expanded according to the methods of the present invention demonstrate a 100-fold to 1000-fold improved efficiency in T cell growth over each stimulation cycle compared with such prior methods.

The large numbers of PBMC feeder cells required can be readily obtained by techniques known in the art, for example by leukaphoresis, which is a standard medical procedure with minimal risks (see, e.g., Weaver et al., *Blood* 82:1981–1984, 1993); and these feeder cells can be stored by cryopreservation in liquid nitrogen until use. LCL can be generated from peripheral blood B cells by transformation with EBV, for example the B95-8 strain of EBV, using standard methods (see, e.g., Crossland et al., *J. Immunol.* 146:4414–20, 1991), or by spontaneous outgrowth in the presence of cyclosporin A. Such LCL cells will grow rapidly and indefinitely in culture for use in the rapid expansion method of the present invention.

Prior to adding feeder cells to the culture vessel, the feeder cells should be prevented from undergoing mitosis. Techniques for preventing mitosis are well known in the art and include, for example irradiation. For example, the PBMC component of the feeder cells can be irradiated with gamma rays in the range of about 3000 to 3600 rads (preferably PBMC are irradiated at about 3300 rads); and the LCL can be irradiated with gamma rays in the range of about 6000–10,000 rads (preferably LCL are irradiated at about 8000 rads).

Since the antigen specificity of the T cell clone is defined prior to expanding the clone in the culture system, either autologous or allogeneic feeder cells can be used to support T cell growth. Rapid expansions of T cells using allogeneic feeder cells are illustrated in several examples below, see, e.g., the expansion of clones from Donor "ER" in Example 1; the expansion of clones from Donors "RRM" and "JTE" in Example 2; and the expansion of clones from Donor "ER" in Example 5. The ability to use allogeneic feeder cells is important in situations in which the patient is infected with a virus that is present in PBMC, e.g., HIV, that could therefore contaminate the T cell cultures. In this circumstances, the use of allogeneic feeder cells derived from an individual that is screened and deemed to be a suitable blood donor by American Red Cross criteria can be used in the culture method.

Most conveniently, the T cell receptor activation signal (normally provided by antigen and antigen-presenting cells) can be achieved by the addition anti-CD3 monoclonal antibodies to the culture system. The anti-CD3 monoclonal antibody most commonly used is OKT$_3$, which is commercially available from Ortho Pharmaceuticals in a formulation suitable for clinical use. The use of αCD3 mAb rather than antigen as a means of ligating the T cell receptor bypasses the need to have a source of antigen-presenting cells, which for virus-specific T cells would require maintaining large numbers of suitable autologous cells and infecting these cells in vitro with high titer virus. As illustrated in Example 6 below, a concentration of anti-CD3 monoclonal antibody of at least about 0.5 ng/ml, preferably at least about 1 ng/ml, more preferably at least about 2 ng/ml, promotes the rapid expansion of the T cells such that a 500- to 3000-fold expansion can be achieved within about 10 to 13 days of growth using the methods of the present invention. Typically, we use a concentration of about 30 ng/ml anti-CD3 monoclonal antibody although, as shown in FIG. 5, much lower concentrations can also be used.

Of course, as an alternative to anti-CD3 monoclonal antibody, the T cell receptors can be activated and the cells stimulated by the addition of antigen-presenting cells, as described in Riddell et al., *J. Immunol.* 146:2795–2904, 1991. Suitable antigen-presenting cells include, for example, viral infected cells, tumor cells, and cells pulsed with the relevant peptide antigen.

The culture media for use in the methods of the invention can be any of the commercially available media, preferably one containing: RPMI, 25 mM HEPES, 25 $\mu$M 2-mercaptoethanol, 4 mM L-glutamine, and 11% human AB serum. Fetal calf serum can be substituted for human AB serum. Preferably, after addition of irradiated feeder cells, anti-CD3 monoclonal antibody, and culture media are added to the target CTL or helper T cell, the mixture is allowed to incubate at 37° C. in a 5% $CO_2$ humidified atmosphere under standard cell culture conditions which are well known in the art. Typically, such conditions may include venting; and addition of $CO_2$ if necessary (e.g., 5% $CO_2$, in a humidified incubator).

Preferably, the medium is also supplemented with interleukin-2 (IL-2). Typically recombinant human IL-2 is used, although a functional equivalent thereof may also be used. preferably, IL-2 is added on day 1, and is re-added at 3–5 day intervals. Thus, we generally add IL-2 on day 1, on day 5 or 6, and again on day 8 or 9. As illustrated in Example 7 below, expansion can be improved by using an IL-2 concentration of at least about 5 U/ml, more preferably at least about 10 U/ml. Generally, we use a concentration of about 30 U/ml.

Significantly, antigen-specific T cells expanded using the methods of the present invention retain their antigen-specific functionality. For example, as illustrated below in Example 8, four different HIV-specific CD8+ cytotoxic T cell clones retained the ability to kill virus-infected cells expressing the relevant antigen (i.e. HIV), and did not acquire non-specific cytolytic activities against irrelevant virus-infected or transformed target cells. Similarly, as illustrated below in Example 9, four different CMV-specific CD8+ cytotoxic T cell clones retained the ability to kill CMV-infected cells, and did not acquire non-specific cytolytic activities against irrelevant virus-infected or transformed target cells.

These characteristics were also applicable to CD4+ helper T cells. Thus, as illustrated below in Example 10, antigen-specific CD4+ T cells propagated using the rapid expansion method of the present invention retained the ability to proliferate in response to the appropriate viral antigens and appropriate antigen-presenting cells (APC).

Furthermore, antigen-specific T cells cultured according to the methods of the present invention are also capable of entering a quiescent, non-dividing phase of the cell cycle; and are capable of remaining viable for at least 4 weeks in vitro. Thus, aliquots of T cells can be removed from the cultures at the end of a stimulation cycle (generally day 12–14), and placed in a culture vessel with a roughly equal number of irradiated PBMC (without anti-CD3 mAb, antigen or IL-2).

The addition of irradiated PBMC as feeder cells improves the ability of the T cells to enter a resting phase and to remain viable. Preferably, the ratio of PBMC feeder cells to resting T cells is at least about 2:1. Without the addition of PBMC feeder cells, viability of the T cells generally drops significantly (typically to levels of about 10% or less).

As described below, the T cells assume a small round morphology and 60–95% remain viable by trypan blue dye exclusion even after 28 days in culture. T cells propagated with the methods of the present invention can also enter a resting phase upon IL-2 withdrawal; and they do not undergo programmed cell death (i.e. apoptosis) upon restimulation via the antigen-specific T cell receptor. Upon restimulation (e.g. with anti-CD3 mAb or antigen), the T cells reacquire responsiveness to IL-2, and can enter the S and $G_2$ phases of the cell cycle and increase in cell number. Such characteristics are believed to be important for in vivo survival of the cells and for the efficacy of adoptive immunotherapy. In contrast, certain previously-described methods for the propagation of T cells have been reported to cause apoptotic cell death in a proportion of cells after cytokine withdrawal or T cell receptor restimulation (see, e.g, Boehme S A and Lenardo M J, *Eur. J. Immunol.*, 23:1552–1560, 1992).

There are a number of different circumstances in which the introduction of functional genes into T cells to be used in immunotherapy may be desirable. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.*, 11:6 (1991); and Riddell et al., Human Gene Therapy 3:319–338 (1992); see also the publications of PCT/US91/08442 and PCT/US94/05601 by Lupton et al., describing the use of bifunctional selectable fusion genes derived from fusing a dominant positive selectable marker with a negative selectable marker.

Various infection techniques have been developed which utilize recombinant infectious virus particles for gene delivery. This represents a currently preferred approach to the transduction of T lymphocytes of the present invention. The viral vectors which have been used in this way include virus vectors derived from simian virus 40 (SV40; Karlsson et al., Proc. Natl. Acad. Sci. USA 84 82:158, 1985), adenoviruses (Karlsson et al., EMBO J. 5:2377, 1986), adeno-associated virus (AAV) (B. J. Carter, Current Opinion in Biotechnology 1992, 3:533–539), and retroviruses (Coffin, 1985, pp. 17–71 in Weiss et al. (eds.), RNA Tumor Viruses, 2nd ed., Vol. 2, Cold Spring Harbor Laboratory, New York). Thus, gene transfer and expression methods are numerous but essentially function to introduce and express genetic material in mammalian cells. Several of the above techniques have been used to transduce hematopoietic or lymphoid cells, including calcium phosphate transfection (Berman et al., supra, 1984), protoplast fusion (Deans et al., supra, 1984), electroporation (Cann et al., Oncogene 3:123, 1988), and infection with recombinant adenovirus (Karlsson et al., supra; Reuther et al., Mol. Cell. Biol. 6:123, 1986), adeno-associated virus (LaFace et al., supra) and retrovirus vectors (Overell et al., Oncogene 4:1425, 1989). Primary T lymphocytes have been successfully transduced by electroporation (Cann et al., supra, 1988) and by retroviral infection (Nishihara et al., Cancer Res. 48:4730, 1988; Kasid et al., supra, 1990; and Riddell, S. et al., Human Gene Therapy 3:319–338, 1992).

Retroviral vectors provide a highly efficient method for gene transfer into eukaryotic cells. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an avian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of several species, including humans. A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell,. or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al. (Cell 33:153, 1983) describe the development of cell lines (e.g., $\Psi 2$) which can be used to produce helper-free stocks of recombinant retrovirus. These cells lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation. Encapsidation in a cell line harboring transacting elements encoding an ecotropic viral envelope (e.g., $\Psi 2$) provides ecotropic (limited host range) progeny virus. Alternatively, assembly in a cell line containing amphotropic packaging genes (e.g., PA317, ATCC CRL 9078; Miller and Buttimore, Mol. Cell. Biol. 6:2895, 1986) provides amphitropic (broad host range) progeny virus. Such packing cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cella nd therefore determines the host range of the retrovirus. The PA 317 cells produce retroviral particles with an amphotropic envelope protein, which can transduce cells of human and other species origin. Other packaging cell lines produce particles with ecotropic envelope proteins, which are able to transduce only mouse and rat cells.

Numerous retroviral vector constructs have been used successfully to express many foreign genes (see, e.g., Coffin, in Weiss et al. (eds.), RNA Tumor Viruses, 2nd ed., vol. 2 (Cold Spring Harbor Laboratory, New York, 1985, pp. 17–71). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles (Coffin, supra, 1985); however, the presence of multiple internal promoters, initially thought to be problematic (Coffin, supra, 1985), was found to be well tolerated in several retroviral constructs (Overell et al., Mol. Cell. Biol. 8:1803, 1983).

Retroviral vectors have been used as genetic tags by several groups to follow the development of murine hematopoietic stem cells which have been transduced in vitro with retrovirus vectors and transplanted into recipient mice (Williams et al., Nature 310:476, 1984; Dick et al., Cell 42:71, 1985; Keller et al., Nature 318:149, 1985). These studies have demonstrated that the infected hematopoietic cells reconstitute the hematopoietic and lymphoid tissue of the recipient animals and that the cells display a normal developmental potential in vivo. The marked cells can be visualized using any of a number of molecular biological techniques which can demonstrate the presence of the retroviral vector sequences, most notably Southern analysis and PCR (polymerase chain reaction). The ability to mark cells genetically using retroviral vectors is also useful in clinical settings in which the technique can be used to track grafts of autologous cells. This approach has already been used to track TILs (tumor-infiltrating lymphocytes) in patients given TIL therapy for terminal cancer treatment by Rosenberg et al. (N. Engl. J. Med. 323:570, 1990). The transduction of these cells with the marker gene was not associated with in vitro cellular dysfunction (Kasid et al., Proc. Natl. Acad. Sci. USA 87:473, 1990).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of coexpressing a dominant selectable marker gene in the vector, thus allowing selection of cells which are expressing specific vector sequences.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., *Cell* 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., *Proc. Natl. Acad. Sci. USA*. 89:33 (1992)).

In addition, it is useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, *Mol. and Cell. Biology* 11:3374–3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT/US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

A variety of methods can be employed for transducing T lymphocytes, as is well known in the art. Typically, we carry out retroviral transductions as follows: on day 1 after stimulation using REM as described herein, we provide the cells with 20–30 units/ml IL-2; on day 3, we replace one half of the medium with retroviral supernatant prepared according to standard methods and then supplement the cultures with 5 µg/ml polybrene and 20–30 units/ml IL-2; on day 4, we wash the cells and place them in fresh culture medium supplemented with 20–30 units/ml IL-2; on day 5, we repeat the exposure to retrovirus; on day 6, we place the cells in selective medium (containing, e.g., an antibiotic corresponding to an antibiotic resistance gene provided in the retroviral vector) supplemented with 30 units/ml IL-2; on day 13, we separate viable cells from dead cells using Ficoll Hypaque density gradient separation and then subclone the viable cells using the rapid expansion method of the present invention.

The lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, CD8+ CD4− cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphcytes and/or helper T lymphocytes) is readily achievable using the rapid expansion method of the present invention, as exemplified herein.

It has also been observed that T cells expanded using REM according to the present invention exhibit very high levels of transduction using vectors such as retroviral vectors which will be of great use in the contexts of adoptive immunotherapy and gene therapy using lymphocytes. The genetic transduction of rapidly-expanded T cells is illustrated in Example 18; and the use of such genetically-transduced antigen-specific CTLs for adoptive immunotherapy in human patients is illustrated in Example 19.

The examples presented below are provided as a further guide to the practitioner of ordinary skill in the art, and are not to be construed as limiting the invention in any way.

Example 1

Rapid Expansion of Human Antigen-Specific Cytotoxic T Lymphocyte Clones and Antigen-Specific Helper T Lymphocytes from 4 Human Donors CD3+, CD8+, CD4− CMV-specific or HIV-specific cytotoxic T cell clones, and CD3+, CD4+, CD8− CMV-specific helper T cell clones were isolated from four human donors that were CMV and/or HIV seropositive (designated "ER", "DRG", "DPN" and "DH"). Ten different antigen-specific T cell clones were isolated using standard methods as described above (and see, e.g., Riddell et al., *Science* 257:238–240 (1992), Riddell et al. (*J. Immunology*, 146:2795–2804, 1991)).

For small-scale expansion, cells were cultured in 25 cm$^2$ tissue culture flasks at an input cell concentration of 5–6× $10^4$ T cells/flask.

For four of the clones (ER3C, ER12C, ER4G, and ER11G), γ-irradiated allogeneic PBMC and LCL were added as feeder cells. Briefly, allogeneic PBMC were obtained by leukaphoresis from a blood bank-screened volunteer donor using standard methods (see, e.g., Weaver et al., supra). Allogeneic LCL were generated from an aliquot of the PBMC by transformation with the B95-8 strain of EBV, as described above. PBMC were subjected to γ-irradiation at 3300 rads and LCL at 8000 rads.

For the remainder of the clones, autologous γ-irradiated PBMC and LCL were added as feeder cells. Autologous PBMC and LCL were isolated and irradiated in the same manner as described for allogeneic feeder cells.

The number of PBMC feeder cells added to each flask was approximately 25×10$^6$, and the number of LCL feeder cells was approximately 5×10$^6$, in a final culture volume of 25 ml. Anti-CD3 monoclonal antibody was added at culture initiation in a final concentration of 30 ng/ml to provide a T cell receptor stimulation signal and human recombinant IL-2 was added on day +1 after culture initiation in a concentration of 40 U/ml to further promote expansion of activated T cells. On days +5 and +8 after culture initiation, one-half the media was replaced with fresh media containing IL-2 at a concentration of 20 U/ml. The cultures were split when the concentration of T cell exceeded 1.5×10$^6$/ml of media. The total number of T cells yielded per flask was evaluated 11–13 days after culture initiation.

The results, as shown in FIG. 1, illustrate that all of the T cells underwent a rapid and dramatic expansion. In particular, the cells exhibited expansions ranging from 866-fold to 1500-fold (with an mean expansion of more than 1100-fold), over a single cycle of stimulation using the methods of the present invention.

Example 2

Large-Scale Expansion of antigen-Specific T Cell Clones From 6 Human Donors for use in Adoptive Immunotherapy CMV- or HIV-specific T cell clones were isolated from 6 individual patients (designated "DRG", "MRL", "DRD", "LAH", "RM" and "JTE"), as described above. Clones were cultured for at least 1 stimulation cycle after transfer from the microwell.

For this large-scale expansion, aliquots of each clone were cultured in 75 cm$^2$ flasks at an input cell number of 1.5×

$10^5$–$5 \times 10^5$ with either autologous (DRG, MRL, DRD, LAH), or allogeneic (RM, JTE) γ-irradiated PBMC and LCL as feeder cells. The numbers of feeder cells added to each flask was 75–90×10$^6$ PBMC and 15×10$^6$ LCL. Anti-CD3 monoclonal antibody was added in a final concentration of 30 ng/ml in a total volume of 75 ml of culture media. Human recombinant IL-2 was added in a final concentration of 30 U/ml on day +1 after culture initiation and one-half the media was replaced with fresh media containing IL-2 (20 U/ml) on days +5 and +8. Cultures were split and re-fed if the T cell concentration exceeded $1.5 \times 10^6$/ml. The total cell yields represent the numbers of cells harvested from the flasks 10–14 days after initiating the cultures and reflect a single cycle of expansion from a small starting cell number.

The results, as shown in FIG. 2, illustrate that rapid large-scale expansions were achieved for all clones. In particular, the clones exhibited expansions ranging from about 250-fold to 2200-fold (with an average expansion of about 1130-fold), over a single cycle of stimulation to yield large populations of antigen-specific T cells (ranging from $6.2 \times 10^8$ to $9 \times 10^9$ cells).

Repetitive cycles of stimulation are also effective in promoting rapid expansion; thus, with this technique it is possible to generate greater than $10^{15}$ clonally-derived effector T cells. In practice, cell doses of $10^9$ to $5 \times 10^{10}$ are more feasible (due to the media and incubator space required for very large scale cultures) and are generally sufficient for use in adoptive immunotherapy.

Example 3
Effect of the Ratio of PBMC Feeder Cells to T Cells in the Rapid Expansion Method Individual 25 cm$^2$ flasks were established with an input cell number of $5 \times 10^4$ T cells from clone DRG28D3 (as in Example 2). A variable number of γ-irradiated PBMC were added to achieve a range of T cell to PBMC ratios of 1:3 to 1:800. Anti-CD3 mAB (30 ng/ml) and $5 \times 10^6$ LCL were added to each flask which contained a final volume of 25 ml. Recombinant IL-2 was added in a concentration of 40 U/ml on day +1 and on days +5 and +8, one-half the media was replaced with fresh media containing IL-2 at a concentration of 20 U/ml. Cultures were split if the concentration of T cells exceeded $1.5 \times 10^6$/ml. The growth of T cells in cultures established at each of the T cell:PBMC ratios was assessed at day +13 by counting viable T cells.

The results, as shown in FIG. 3, indicate that growth of the T cell can be markedly enhanced by using T cell:PBMC ratios of at least 1:40 (i.e. at least a 40-fold excess of PBMC), preferably at least 1:200, still more preferably between about 1:400 and 1:800. Typically, we use a ratio of about 1:500.

Example 4
Effect of the Use of LCL Feeder Cells in the Rapid Expansion Method

Individual 25 cm$^2$ flasks were established with an input cell number of $5 \times 10^4$ T cells from clone DRG28D3 (as in Example 2). A variable number of γ-irradiated LCL were added to achieve a range of T cell to LCL ratios of 1:0 to 1:300. Anti-CD3 mAB (30 ng/ml) and $25 \times 10^6$ PBMC were added to each flask which contained a final volume of 25 ml. Recombinant IL-2 was added in a concentration of 40 U/ml on day +1 and on days +5 and +8, one-half of the media was replaced with fresh media containing IL-2 at a concentration of 20 U/ml. Cultures were split if the concentration of T cells exceeded $1.5 \times 10^6$/ml. The growth of T cells in cultures established at each of the T cell:LCL ratios was assessed at day +13 by counting viable T cells.

Figure 4:
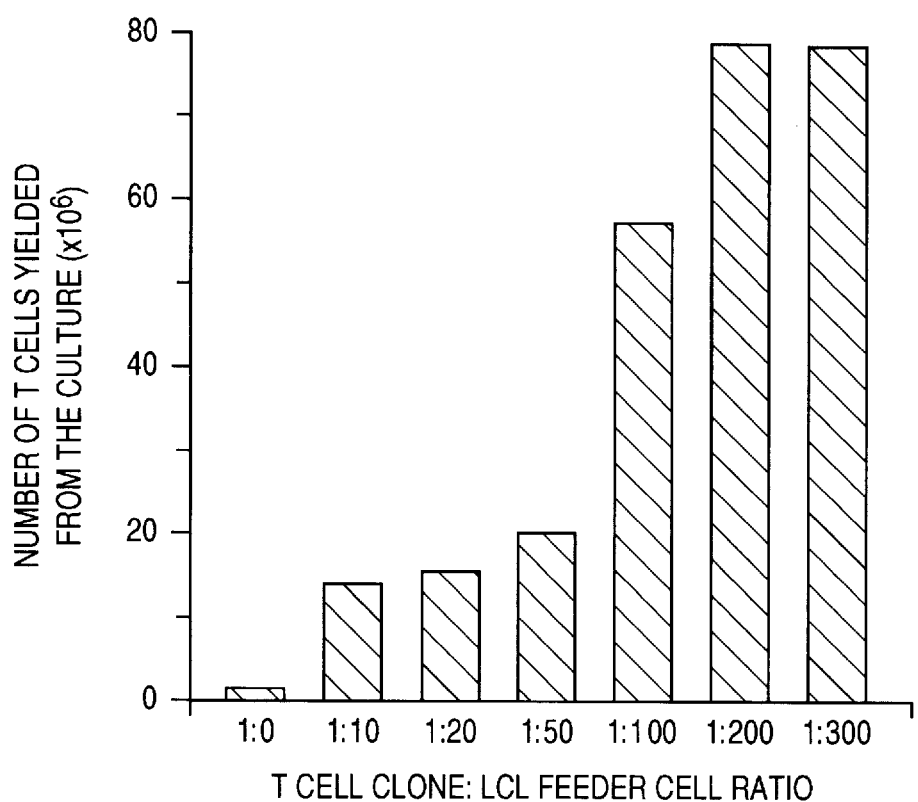
FIG. 4 is an illustration of the effect of the use of LCL feeder cells in the rapid expansion method, as described in Example 4.

The results, as shown in FIG. 4, indicate that the expansion rates under REM can be further elevated by adding LCL feeder cells to the culture. Such additional enhancement can be achieved using T cell:LCL ratios of at least 1:10 (i.e. at least a 10-fold excess of PBMC), preferably at least 1:20, still more preferably between about 1:50 and 1:200. Typically, we use a ratio of about 1:100.

Example 5
Comparison of the Rapid Expansion Method with Other Methods Used for the Propagation of T Cells Aliquots of six different T cell clones were stimulated under the conditions described below.

(a) Using REM

Following the rapid expansion method of the present invention, $5 \times 10^4$ T cells were cultured in a 25 cm$^2$ flask, with γ-irradiated PBMC at a T cell:PBMC ratio of 1:500, and γ-irradiated LCL at a T cell:LCL ratio of 1:100, in 25 ml media containing 40 ng/ml αCD3 mAB. Recombinant IL-2 (30 U/ml) was added on day +1, and one-half of the media was replaced with fresh media containing IL-2 (20 U/ml) on days +5 and +8. Cultures were split when the concentration of T cells exceeded $1.5 \times 10^6$/ml. The fold expansion in cell number was determined by dividing the total number of viable T cells obtained 11 days after culture initiation by the starting cell number.

(b) Using Standard αCD3 Stimulation

Following essentially the methods described by Riddell et al. (*J. Immun. Methods,* 1990, supra), $5 \times 10^5$ T cells were cultured in individual wells of a 24-well plate with $2 \times 10^6$ γ-irradiated PBMC and $2 \times 10^5$ γ-irradiated LCL in 2 ml media containing 40 ng/ml αCD3 mAB. Recombinant IL-2 (30 U/ml) was added on day +1 and one-half of the media was replaced with fresh media containing IL-2 (20 U/ml) on days +5 and +8. Cultures were split when the concentration of T cells exceeded $1.5 \times 10^6$/ml. The fold expansion in cell number was determined by dividing the total number of viable T cells obtained 11 days after culture initiation by the starting cell number.

(c) Using Standard Antigen Stimulation

Following essentially the method described by Riddell et al. (*J. Immunol.,* 1991, supra), $5 \times 10^5$ T cells were cultured in individual wells of a 24-well plate with specific antigen consisting of $5 \times 10^4$ autologous CMV-infected fibroblasts, and feeder cells consisting of $2 \times 10^6$ γ-irradiated PBMC and $2 \times 10^5$ γ-irradiated LCL in 2 ml media. Recombinant IL-2 (30 U/ml) was added on day +2 and one-half of the media was replaced with fresh media containing IL-2 (20 U/ml) on days +4 and +6. Cultures were split when the concentration of T cells exceeded $1.5 \times 10^6$/ml. In cultures stimulated with antigen, maximal cell yields were obtained between day +7 and day +9 after culture initiation; thus, the fold expansion in cell number was determined by dividing the total number of viable T cells obtained 7–9 days after culture initiation by the starting cell number.

The comparative results, shown in FIG. 5, indicate that there is a dramatic expansion over a single cycle of stimulation using the rapid expansion method (REM) of the present invention as compared to conventional methods of propagating T cells. In particular, the average expansion using REM was almost 100-fold higher than that observed using the standard anti-CD3 method, and almost 500-fold higher than that observed using the standard antigen stimulation method.

Example 6
Effect of the Addition of Anti-CD3 Monoclonal Antibody to the Rapid Expansion Cultures In order to assess the effect of adding anti-CD3 monoclonal antibody to the culture system, $5 \times 10^4$ T cells (derived from clone DRG 28D3 as in Example 2) were cultured in a 25 cm$^2$ flask with γ-irradiated PBMC at a T cell:PBMC ratio of 1:500 and γ-irradiated LCL at a T cell:LCL ratio of 1:100 in 25 ml media containing various concentrations of anti-CD3 mAB at a range of concentrations from 0–40 ng/ml. Recombinant IL-2 (30 U/ml) was added on day +1 and one-half the media was replaced with fresh media containing IL-2 (20 U/ml) on days +5 and +8. Cultures were split when the concentration of T cells exceeded $1.5 \times 10^6$/ml. T cell growth was assessed by counting the number of viable cells obtained 11 days after culture initiation.

Figure 6:
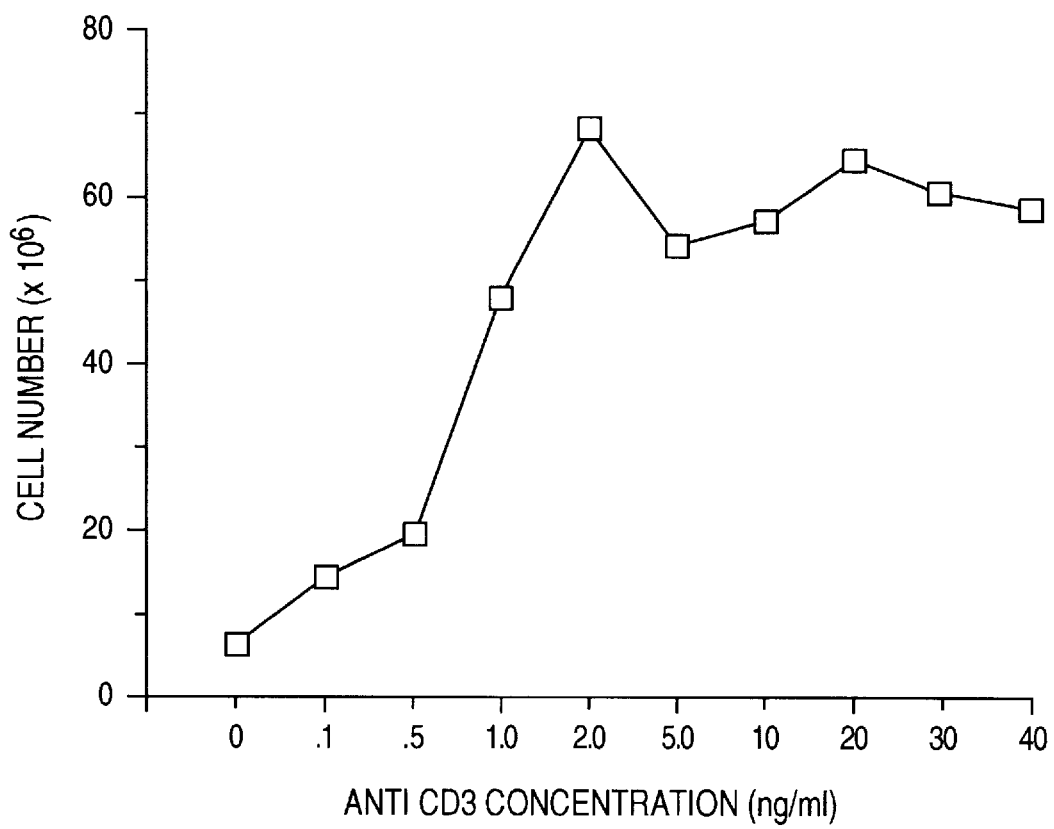
FIG. 6 is an illustration of the effect of the addition of anti-CD3 monoclonal antibody to the rapid expansion cultures, as described in Example 6.
Figure 7:
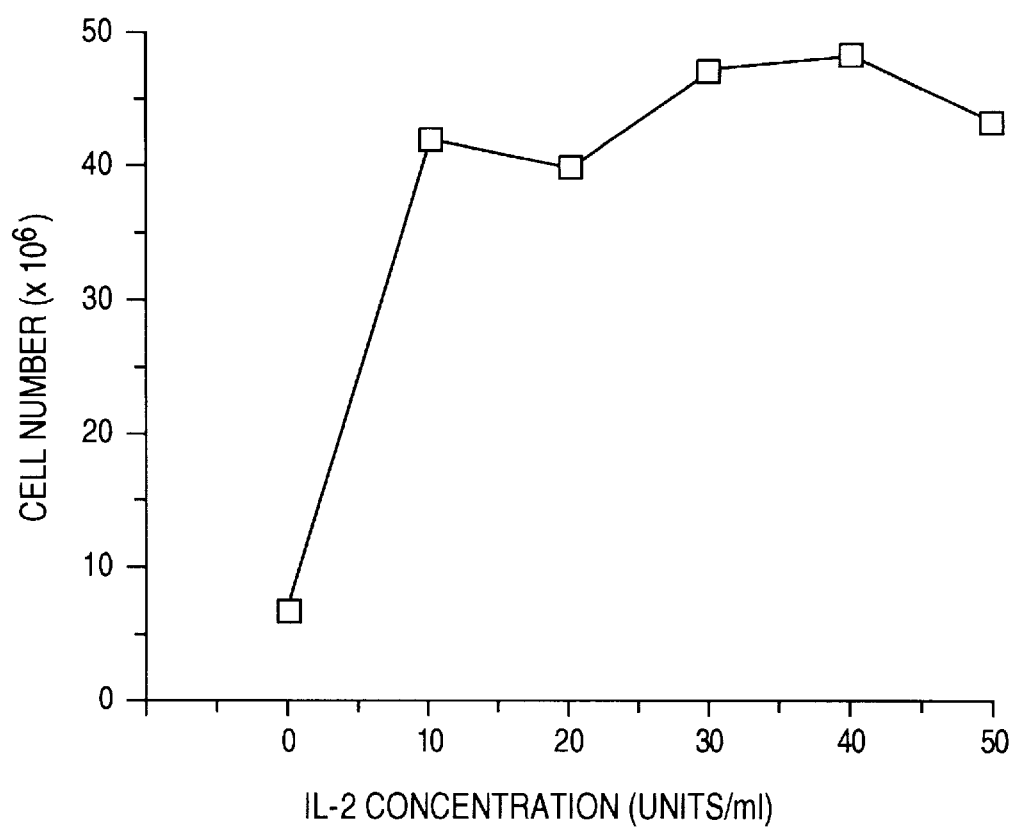
FIG. 7 is an illustration of the effect of the addition of IL-2 to the rapid expansion cultures, as described in Example 7.

The results, as shown in FIG. 6, indicate that the expansion rates under REM can be further elevated by adding anti-CD3 monoclonal antibody to the culture. Such additional enhancement can be achieved using anti-CD3 concentrations of at least about 0.5 ng/ml, preferably at least about 1 ng/ml, more preferably at least about 2 ng/ml. Typically, we use a concentration of about 30 ng/ml.

Example 7
Effect of the Addition of IL-2 to the Rapid Expansion Cultures

In order to assess the effect of adding anti-CD3 monoclonal antibody to the culture system, $5 \times 10^4$ T cells (derived from clone DRG 28D3 as in Example 2) were cultured in a 25 cm$^2$ flask with γ-irradiated PBMC at a T cell:PBMC ratio of 1:500 and γ-irradiated LCL at a T cell:LCL ratio of 1:100 in 25 ml media containing 30 ng/ml of anti-CD3 mAB. Recombinant IL-2 was added in various concentrations (ranging from 0 to 50 U/ml) to each flask on day +1, and then on days +5 and +8 one-half of the media was replaced with fresh media containing IL-2 at the same concentration. Cultures were split when the concentration of T cells exceeded $1.5 \times 10^6$/ml. T cell growth was assessed by counting the number of viable cells obtained 11 days after culture initiation.

The results, as shown in FIG. 6, indicate that the expansion rates under REM can be further elevated by adding IL-2 to the culture. Such additional enhancement could be achieved using IL-2 concentrations of at least about 5 U/ml, preferably at least about 10 U/ml. Typically, we use a concentration of about 30 U/ml.

Example 8
HIV-Specific CD8+ Cytotoxic T Lymphocytes Retain Antigen-Specific Lytic Functions After Rapid Expansion Clones RM56G6/7, RM56G6/2, JTE10A5/5 and JTE10A5/13 are CD3+, CD8+, CD4−, HIV(gag)-specific cytotoxic T cell clones, generated as described in Riddell et al. *J. Immunol.*, 1991 (see Example 2). Individual clones were cultured for at least 2 cycles of stimulation using the rapid expansion culture method of the present invention. Ten to 12 days after stimulation, the T cell clones were assayed for retention of MHC restricted Ag-specific cytolytic functions in a 5 hour Cr$^{51}$ release assay as described by Riddell, S., et al., *J. Immunol.*, 1991, supra.

Target cells consisted of autologous and HLA-mismatched EBV-transformed LCL, and were either mock infected ("mock") or infected for 16 hours with a vaccinia-HIV(gag) recombinant virus ("Vac/gag") or a control vaccinia virus ("Vac").

The results, as shown in FIG. 8, demonstrate that HIV(gag)-specific CTL clones, expanded using REM, retain the ability to lyse HIV(gag)-expressing target cells in an MHC-restricted manner.

Example 9
CMV-Specific CD8+ Cytotoxic T Lymphocytes Retain Antigen-Specific Lytic Functions After Rapid Expansion Clones LAH4F8, LAH7E4, MRL10E6 and MRL10B5 are CD3+, CD8+, CD4−, CMV-specific cytotoxic T cell clones generated as described in Example 2. Individual clones were cultured for at least 2 cycles of stimulation using the rapid expansion culture method of the present invention. Ten to 12 days after stimulation the T cell clones were assayed for retention of MHC restricted Ag-specific cytolytic function in a 5 hour Cr$^{51}$ release assay, as described above.

Target cells consisted of autologous and HLA-mismatched fibroblasts, and were either mock infected ("mock") or infected for 24 hours with AD169 strain of CMV ("CMV").

The results, as shown in FIG. 9, demonstrate that CMV-specific CTL clones, expanded using REM, retain the ability to lyse CMV-expressing target cells in an MHC-restricted manner.

Example 10
CMV-Specific CD4+ Helper T Lymphocytes Retain Antigen-Specific Proliferation Functions After Rapid Expansion in Vitro T cell clones DHTh-2 and DHTh-10 (see Example 1) are CD3+, CD4+, CD8− CMV-specific class II MHC-restricted clones generated from a CMV-seropositive donor by stimulation of PBL with CMV antigen and cloning by limiting dilution as described above.

Aliquots of these clones were expanded for 2 cycles of stimulation with the rapid expansion method of the present invention using anti-CD3 mAb at 30 ng/ml and a 1:500 ratio of T cells to PBMC and a 1:100 ratio of T cells to LCL.

Fourteen days after cycle 2, the T cells were washed and plated at $5 \times 10^4$ cells/well in triplicate cultures in 96 well round bottom plates. Irradiated PBMC obtained from donor DH or from a class II MHC mismatched allogeneic donor were added at $5 \times 10^5$ as antigen presenting cells. To some triplicates, CMV antigen, prepared by glycine extraction, was added in a concentration of 1/500. Wells were pulsed with $^3$H thymidine for the final 18 hours of a 96 hour incubation and the cells harvested for β scintillation counting.

Figure 10A:
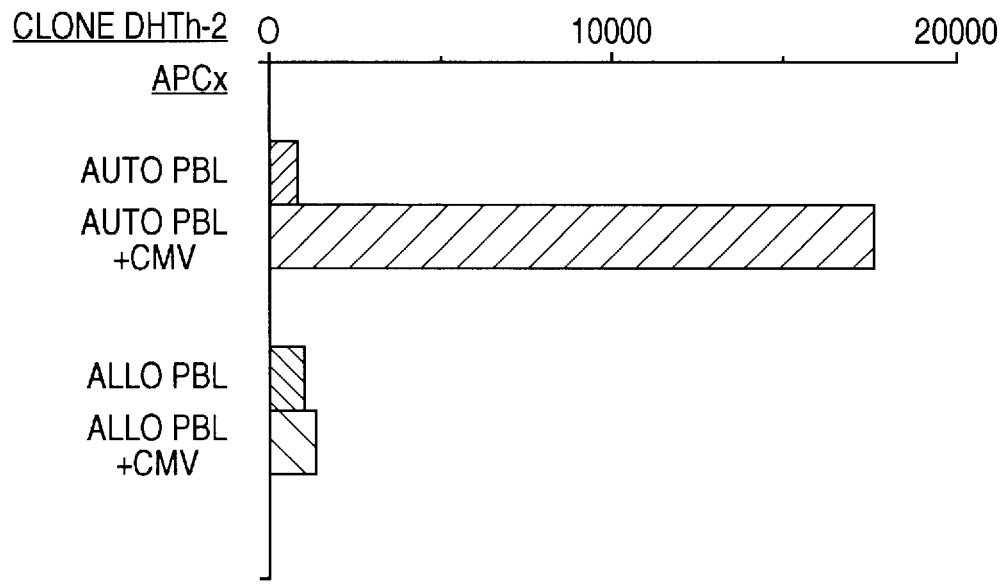
FIG. 10 is an illustration of data showing that CMV-specific CD4+ helper T lymphocytes retain antigen-specific proliferation functions after rapid expansion in vitro, as described in Example 10.
Figure 10B:
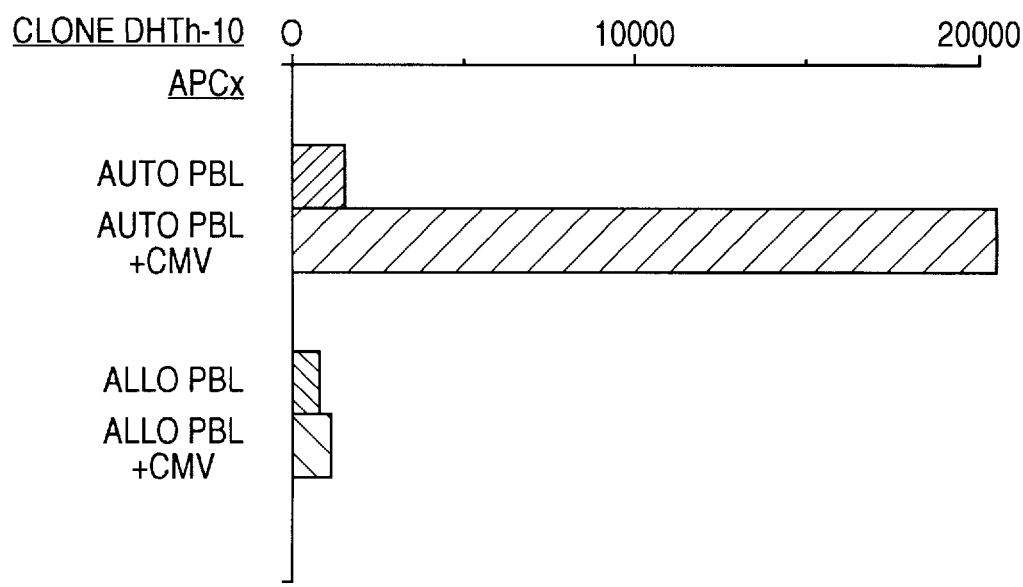

The data, shown in FIG. 10, confirm that clones DHTh-2 and DHTh-10 continued to exhibit MHC-restricted CMV-specific proliferative responses after rapid in vitro expansion using REM.

Example 11
Rapidly Expanded T Cells Retain the Ability to Enter a Resting Stage Upon Cytokine Withdrawal, they Remain Viable in Vitro Without Antigen or IL-2, and they Regain Responsiveness to IL-2 Upon T Cell Receptor Activation Antigen-specific T cells cultured according to the methods of the present invention are also capable of entering a quiescent, non-dividing phase of the cell cycle; and are capable of remaining viable for at least 4 weeks in vitro. Thus, aliquots of T cells can be removed from the cultures at the end of a stimulation cycle (generally day 12–14), and placed in a culture vessel with a roughly equal number of irradiated PBMC (without anti-CD3 mAb, antigen or IL-2). The addition of irradiated PBMC as feeder cells improved the ability of the T cells to enter a resting phase and to remain viable. Moreover, the T cells were observed to assume a small round morphology and 60–95% of the cells remained viable (as determined by trypan blue dye exclusion) even after 28 days in culture.

Clone ER11G (see Example 1) is a representative CD3+, CD8+, CD4− HIV(gag)-specific cytotoxic T cell clone that was propagated for two cycles with the rapid expansion method. Following the second cycle of growth, the T cells were rested in vitro. Briefly, the cells were washed, resuspended in fresh media at a cell concentration of $1 \times 10^6$/ml, and then 1 ml was plated into individual wells of a 24 well plate. $2 \times 10^6$ γ irradiated allogeneic PBMC were added to each well in a final volume of 2 ml. One-half volume of fresh media was added every 7 days.

After 21 days, cells were separated over Ficoll hypaque and viable resting T cells were washed and plated in triplicate cultures at $1 \times 10^5$/well in 96 well round bottom plates. 0, 2.5, 5, 10 or 20 units/ml of IL-2 were added to assess responsiveness of resting cells to IL-2. An aliquot of the T cells were activated for 48 hours with anti-CD3 mAb and then plated in 96 well round bottom plates as described above. To assess proliferation, all wells were pulsed with $^3$H thymidine for the final 16 hours of a 72 hour incubation.

Figure 11:
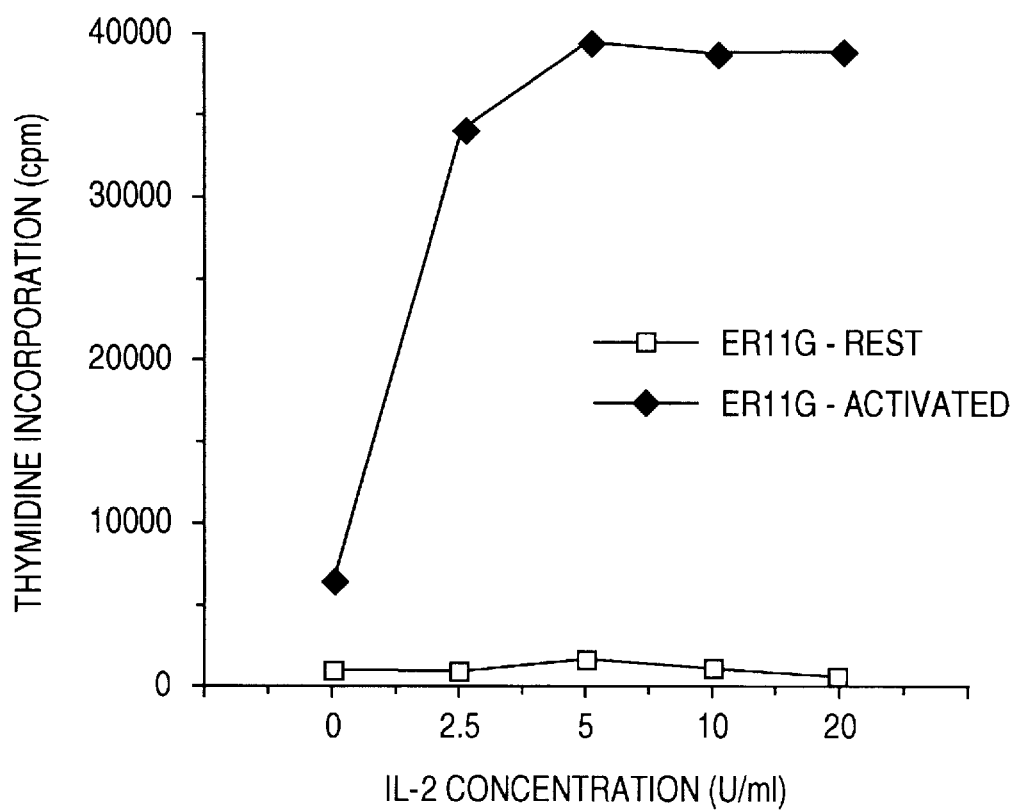
FIG. 11 is an illustration of data showing that rapidly expanded T cells retain the ability to enter a resting stage upon cytokine withdrawal, they remain viable in vitro without antigen or IL-2, and they regain responsiveness to IL-2 upon T cell receptor activation, as described in Example 11.

The data, shown in FIG. 11, confirmed that during the quiescent stage, T cells generated by REM according to the present invention did not proliferate in response to exogenous IL-2; and they regained IL-2 responsiveness upon activation of the T cell receptor.

Example 12
Rapidly Expanded T Cells Enter the G0/G1 Stage of the Cell Cycle After in Vitro Rest and do not Express the IL-2R α Chain T cell clone DRG28D3 (see Example 2) is a representative CD3+, CD8+, CD4− CMV-specific cytotoxic T cell clone that was propagated for two cycles with the rapid expansion method. After the second cycle of expansion, the cells were rested in vitro as described in Example 11. After 14 days of in vitro rest, viable T cells were separated over Ficoll hypaque and washed.

Figure 12:
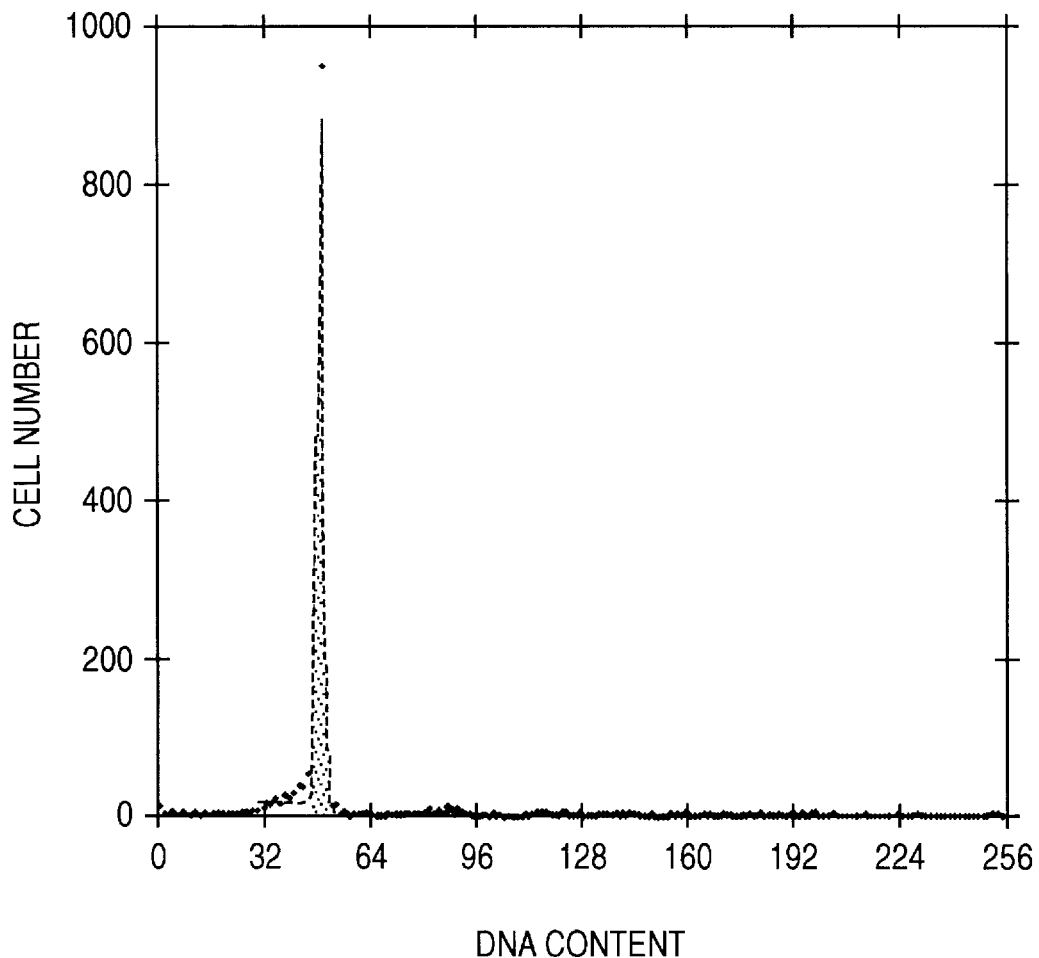
FIG. 12 is an illustration of data showing that rapidly expanded T cells enter the G0/G1 stage of the cell cycle after in vitro rest and do not express the IL-2R α chain, as described in Example 12.

Cell cycle analyses were then performed by staining the cells with propidium iodide to assess DNA content. The data, shown in FIG. 12, indicated that approximately 95% of the cells had entered the G0/G1 phase of the cell cycle.

Expression of the IL-2 receptor a chain was monitored by staining the cells using indirect immunofluorescence with an anti-CD3 monoclonal antibody, an anti-IL2 receptor α-chain monoclonal antibody, or only the second step monoclonal antibody. The data indicated that the resting cells were stained with the anti-CD3 antibody, but expressed very low of the IL-2 receptor a chain. As a positive control, T cells that had been activated for 48 hours were also stained. The data showed that the low level expression of IL2Rα on resting T cells was up-regulated upon activation.

Example 13
Resting T Cells are Induced into the S and G2/M Phases of Cell Growth After T Cell Receptor Activation An aliquot of DRG28D3 cells that had been rested for 14 days as described above, were re-stimulated using the rapid expansion method. Briefly, $1 \times 10^5$ T cells were cultured in a 25 cm$^2$ flask with $25 \times 10^6$ γ-irradiated PBMC and $5 \times 10^6$ γ-irradiated LCL as feeder cells, and 30 ng/ml of anti CD3 mAB. On day +1, 30 U/ml IL-2 was added. On day +5, the culture was harvested and the cells were centrifuged over Ficoll hypaque to separate residual feeder cells from T cells. The remaining cells were then washed and stained with propidium iodide to access DNA content.

Figure 13:
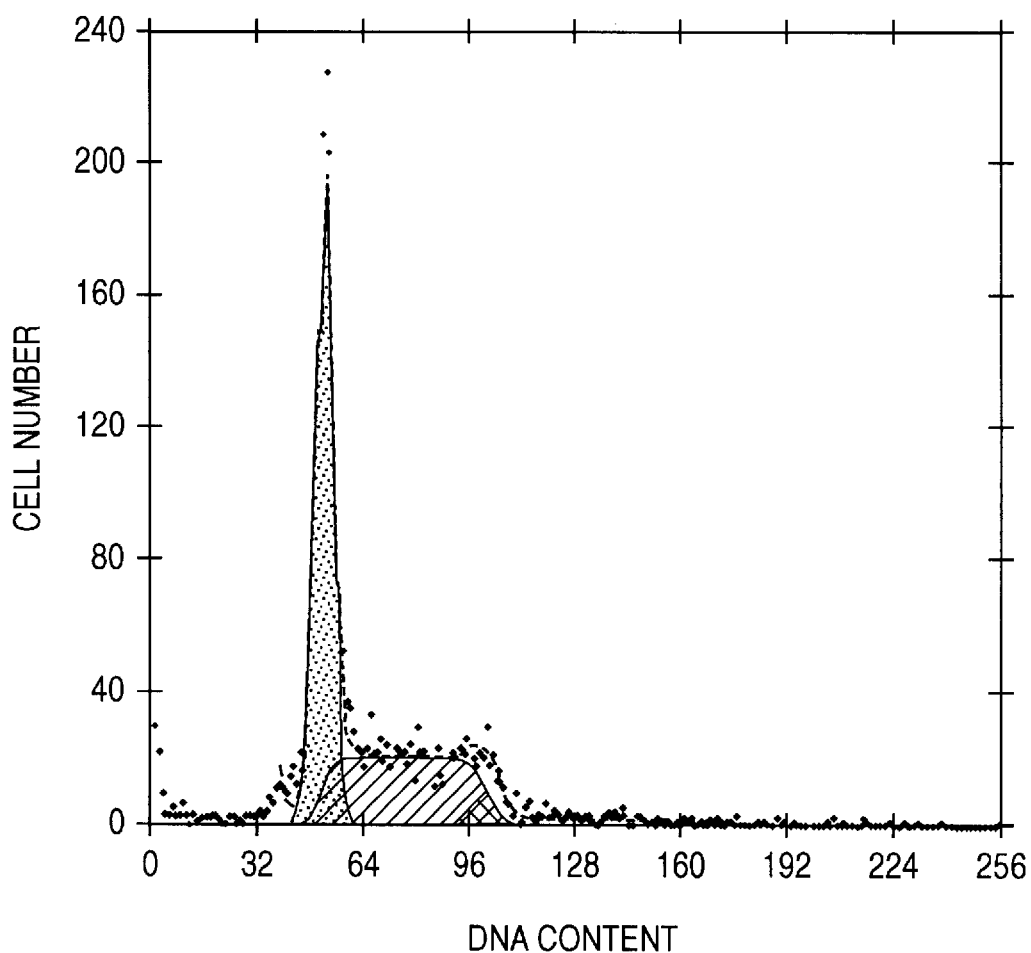
FIG. 13 is an illustration of data showing that resting T cells are induced into the S and G2/M phases of cell growth after T cell receptor activation, as described in Example 13.

The results, shown in FIG. 13, indicate that at this time following activation, about 40% of the T cells had entered the S or G$_2$/M phases of the cell cycle with the remaining cells in G1.

Summarizing the above data, T cells propagated with the methods of the present invention can enter a resting phase upon IL-2 withdrawal; and they do not undergo programmed cell death (i.e. apoptosis) upon restimulation via the antigen-specific T cell receptor. Upon restimulation (e.g. with anti-CD3 mAb or antigen), the T cells reacquire responsiveness to IL-2, and can enter the S and G$_2$ phases of the cell cycle and increase in cell number. Such characteristics are believed to be important for in vivo survival of the cells and for the efficacy of adoptive immunotherapy.

Example 14
Isolation of Polyclonal Antigen-Specific T Cells and Generation of CMV-Specific CTL Clones The methods described herein are particularly useful for rapidly propagating T cells, including human antigen-specific T cell clones, for use in adoptive immunotherapy. In the circumstance where T cell clones of defined antigen specificity are to be used in therapy, these clones must first be isolated from polyclonal T cells using standard methods, illustrated below. The antigen-specific T cell clones can then be rapidly expanded in number using the rapid expansion methods of the present invention. In the following example of how this culturing method is used, the generation of T cell clones using standard methods is briefly described.

Peripheral blood (PB) was taken from a person designated "MRL" known to have previously been infected with cytomegalovirus (CMV) by virtue of CMV sero-positivity. Peripheral blood from MRL was purified to obtain a population of peripheral blood mononuclear cells (PBMC) using Ficoll-hypaque density gradient separation.

Fibroblast cell lines were derived from a skin biopsy obtained from donor MRL. The autologous fibroblasts ($5 \times 10^5$) were infected with AD169 strain cytomegalovirus (CMV) for six hours and then added in a 1:20 ratio to autologous PBMC ($1 \times 10^7$). After 7 days of culture, CD4+ T cells were depleted from the population and the CD8+ T cells cloned by plating 0.3–0.7 T cells/well in 96-well round-bottom wells with $2 \times 10^3$ AD169 CMV-infected fibroblasts; $5 \times 10^4$ γ-irradiated PBMC; $1 \times 10^4$ γ-irradiated LCL; and 50 units/ml recombinant human IL-2 in a fixed volume of 0.2 ml culture media. Aliquots of T cells in wells positive for growth 13 days after plating were tested for virus-specific cytolytic activity as described by Riddell et al., *J. Immunol.*, supra, and those exhibiting cytolytic activity were then transferred to microwells for restimulation or to 25 cm$^2$ flasks for rapid expansion.

Example 15
Rapid Expansion of CD8+ CMV-Specific T Cell Clones Using an Autologous Feeder Cell System The MRL CD8+ CMV-specific T cell clones (from Example 14) were counted and placed in a tissue culture flask. Autologous PBMCs were obtained by leukophoresis of the donor and were γ-irradiated and then added as feeder cells. The PBMCs were irradiated with γ-rays at 3,300 rads. The ratio of irradiated PBMC to the amount of target T cells was in the range of 400:1 to 700:1, generally about 500:1.

The media used in these cultures was RPMI supplemented with 25 mM HEPES, 11% human CMV-seronegative AB serum, 4 mM L-glutamine, and 25 µM 2-mercaptoethanol. Anti-CD3 monoclonal antibody (30 ng/ml) was added to the culture mixture at the initiation of the rapid expansion culture. The cultures were then fed with IL-2 at a concentration of 30 units/ml on day +1 after initiation, and again on day +5, and again on day +8. Also, on day +5 and day +8, the target T cells were counted, and if the concentration of T cells exceeded $1 \times 10^6$/ml, the culture was split to reduce the concentration of T cells to about $2.5 \times 10^5$ to $5 \times 10^5$ per ml of culture media. After day +10, the target T cells underwent quality control testing prior to use in adoptive immunotherapy, or were restimulated by repeating the steps outlined above for further expansion and subsequent use in immunotherapy.

With the MRL clones, expansions of approximately 2000-fold were obtained within a 10–13 day period. In general, 500-fold to 3000-fold expansions can be achieved within a 10–13 day culture period. Thus, even starting from $2\times10^4$–$5\times10^5$ T cells, the rapid expansion culture method can yield up to $5\times10^8$ T cells for each clone after a single cycle of stimulation. Thus, using REM, it is routinely possible to achieve clonal populations of greater than $5\times10^9$ T cells after two 10–13 day cycles of growth.

Example 16
Adoptive Immunotherapy in Human Patients Using T Cell Clones Propagated by REM The rapid expansion method has now been applied to more than 100 different clones from ten different individuals. The efficacy of adoptive immunotherapy using T cell clones propagated by REM has been evaluated in studies conducted at the Fred Hutchinson Cancer Research Center in conjunction with the University of Washington School of Medicine. The studies were designed to determine if adoptive transfer of REM-generated T cell clones can restore antigen-specific responses in bone marrow transplant ("BMT") recipients.

By way of illustration, in one such study, CMV-specific CD8+ T cell clones were derived from Donor "MRL", were rapidly expanded using REM as described herein, and were then administered to the HLA-identical sibling who had received an allogeneic bone marrow transplant from Donor MRL. The T cell administrations were initiated 35 days after the bone marrow transplant, and doses were given every week for four consecutive weeks. For the first two doses, the antigen-specific T cells were expanded as described in Example 1. For the third and fourth doses, the T cells were expanded as described in Example 2.

The T cell clones were administered in 4 intravenous infusions beginning at a cell dose of $3.3\times10^7$ cells/ml and escalating with each infusion as follows: infusion #2 —$1.0\times10^8$ T cells/m$^2$; infusion #3 —$3.3\times10^8$ cells/m$^2$; and infusion #4 —$1\times10^9$ T cells/m$^2$.

Prior to and after each adoptive transfer of CD8+ CMV-specific T cell clones, PBMC were obtained from the recipient, stimulated in vitro with HLA-matched, CMV-infected fibroblasts and tested for the presence of CD8+ CMV-specific CTL activity (as described in Examples 8–9) or stimulated in vitro with CMV antigen to test for CD4+ CMV-specific helper T cell activity, using the method described in Example 10.

Figure 14A:
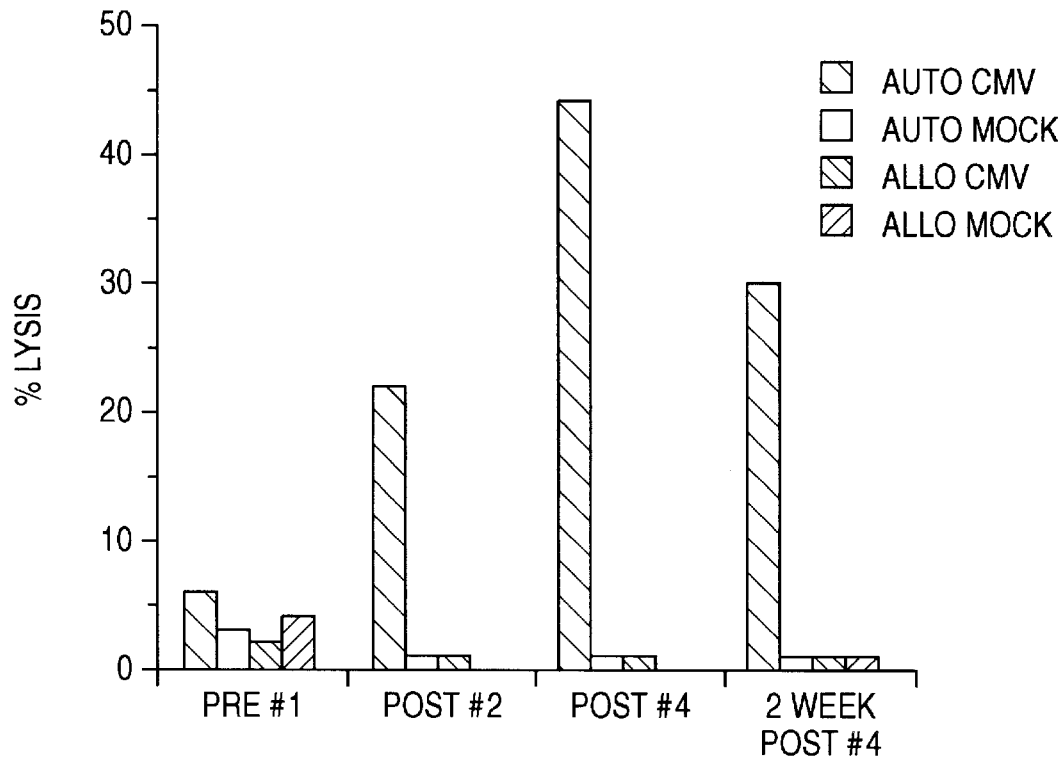
FIG. 14A and 14B is an illustration of data demonstrating adoptive immunotherapy in human patients using T cell clones propagated by REM, as described in Example 16.
Figure 14B:
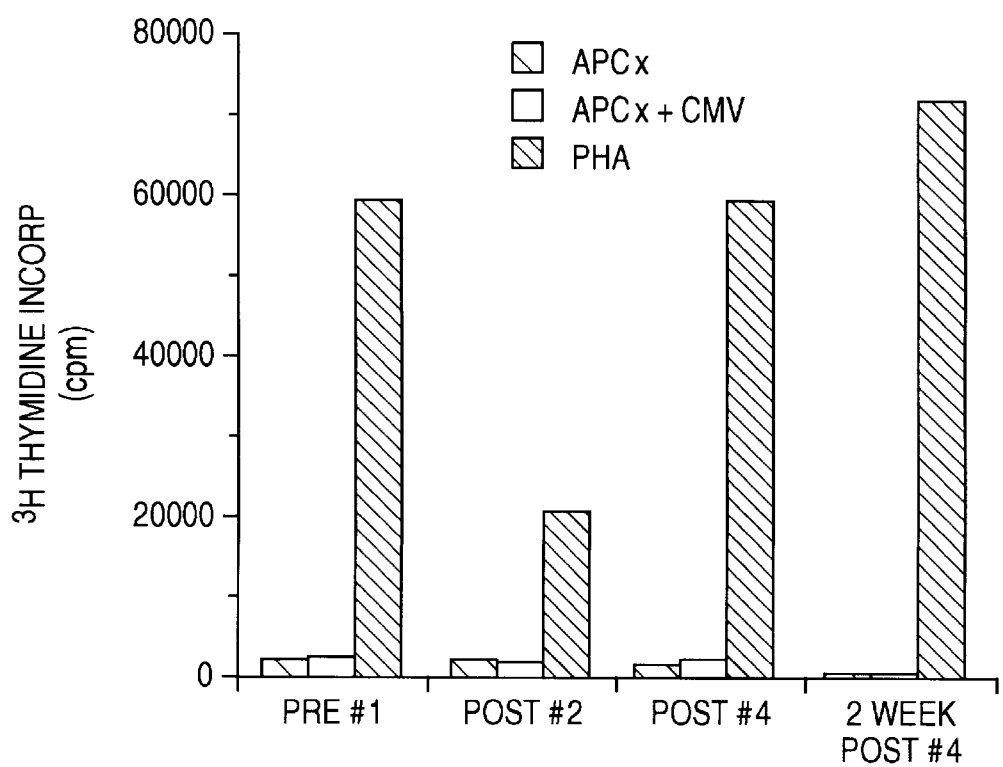

As shown in FIG. 14A, the patient's CD8+ CMV-specific CTL response was essentially negative prior to initiating T cell infusions, but a large increase in the CMV-specific cytolytic activity was observed after the administration of the rapidly expanded CTLs (as expected, CD4+ CMV-specific helper T cell responses were not affected, FIG. 14B).

These demonstrations of the use of REM-expanded antigen-specific T cell clones in adoptive immunotherapy in human recipients have now been repeated in a number of similar studies at the Fred Hutchinson Cancer Research Center in conjunction with the University of Washington School of Medicine.

Example 17
Use of Allogeneic Feeder Cells in the Rapid Expansion System

In some circumstances the use of autologous PBMC and LCL as feeder cells may be contraindicated, such as in the case of an HIV-infected individual where the feeder cells may harbor HIV and may thus transmit the virus to the culture. In such a situation, allogeneic irradiated PBMC and LCL can be used in the culture system in place of autologous PBMC and LCL.

As an illustrative example of the use an allogeneic feeder cell system, cryopreserved allogeneic PBMC were obtained from Donor "RRM" (who met American Red Cross criteria for blood donation). The PBMC were γ-irradiated and were added in conjunction with γ-irradiated allogeneic LCL (derived from the same donor by standard methods as described above), as feeder cells. We used ratios of allogeneic PBMC and LCL to target T cells that were roughly the same as for the autologous system i.e., 400–700:1 for PBMC, and 20–120:1 for LCL.

The cells to be targeted for expansion were CD8+ HIV-specific CTL derived from an HIV sero-positive donor. In particular, CD8+ HIV(gag)-specific CTL were generated from a sample of PBMC obtained from an HIV seropositive individual "ER" by first separating cells based on their adherence to plastic and then infecting the adherent monolayer with a vaccinia/gag recombinant virus for 16 hours. The vac/gag-infected adherent cells were then subjected to UV light to inactivate the vaccinia virus and the nonadherent cells containing the responding T cells were added. After 7 days, this stimulation was repeated and IL-2 2–5 U/ml was added 2 and 4 days after restimulation. After a further 7 days, the residual CD4+ T cells were depleted from the culture and CD8+ T cells were plated at 0.3–0.5 cells/well in 96-well round-bottom plates containing αCD3 mAb (30 ng/ml), irradiated allogeneic PBMC ($5\times10^4$/well), irradiated allogeneic LCL ($1\times10^4$/well), IL-2 (50 units/ml) and 0.2 ml culture media. After 14 days, growing clones were screened for cytolytic activity against autologous HIV-gag expressing target cells and positive clones were transferred to 25 cm$^2$ flasks for rapid expansion as described above.

The range of expansion over a single cycle of stimulation of CD8+ HIV(gag)-specific T cell clones was similar to that observed in the autologous feeder cell system illustrated in Example 15; that is, there was a 500–1500 fold expansion, and the clones retained HIV(gag)-specific cytolytic reactivity.

Example 18
Genetic Transduction and Rapid Expansion of Human T Cell Clones for Use in Adoptive Immunotherapy The rapid expansion method of the present invention can be used to promote the stable transfer of genes encoded in retroviral vectors into human T cells.

As an illustrative example, HIV(gag)-specific T cell clones derived from donor "RRM" were stimulated under the culture conditions described above and were fed with IL-2 on day +1 after stimulation.

On day +3 after stimulation, one-half the media was replaced with a retroviral supernatant, termed "HyTK", containing retroviral particles encoding as a fusion gene the hygromycin phosphotransferase gene and the Herpes simplex virus thymidine kinase gene (as described by Lupton et al., supra). The cultures were then supplemented with 5 μg/ml of polybrene and 20 U/ml IL-2. The following day (day +4) the cells were washed and placed in CTL media with 20 U/ml of IL-2. On day +5, exposure to the retroviral supernatant was repeated as described above and on day +6, the cells were placed in media containing hygromycin at a concentration of 250 ug/ml and IL-2 at 30 U/ml. On day +13 after stimulation, the viable cultured T cells were separated from dead cells by Ficoll Hypaque density gradient separation and then subcloned in 96-well round bottom plates at 1 cell/well with irradiated PBMC and LCL as feeder cells, anti-CD3 monoclonal antibody (30 ng/ml) and IL-2 (50 U/ml). The advantage of subcloning the T cells is that the resulting gene-modified T cells have a single integration site and can be evaluated individually for mutational events that might affect growth and/or function. (Alteratively, the transduced clones need not be subcloned but can be restimulated under conditions of an additional cycle of hygromycin selection to ensure that transduced T cells are negatively selected.).

Seven days after plating, hygromycin B was added to the wells at 250 µg/ml to select subclones that expressed HyTK. These gene-modified subclones were then rapidly expanded in 25 cm² or larger flasks using the rapid expansion method described above.

These experiments have revealed that highly efficient transduction can be achieved by transducing cells that are rapidly expanding according to the methods described herein. It is believed that the ability of the T cell clones expanded by REM to efficiently progress into the S phase of the cell cycle greatly enhances the efficiency with which the T cell clonal lines are transduced with vectors such as retroviral vectors.

The resulting genetically-transduced HIV(gag)-specific CTLs were used for human adoptive immunotherapy, as described in the following example.

Example 19
Adoptive Immunotherapy Using Genetically-Transduced Antigen-Specific CTL Genetically-transduced antigen-specific CTL prepared as in Example 18 were used in adoptive transfer experiments performed in patient "RRM". In particular, individual HyTK-transduced HIV(gag)-specific subclones derived from clone RRM56G6 were expanded by the culture method described herein and were infused intravenously in 4 infusions given 2 weeks apart. The T cells were administered in 4 doses 2 weeks apart as follows: dose #1—1×10⁸ cells/m²; dose #2—3.3×10⁸ cells/m²; dose #3—1×10⁹ cells/m²; dose #4—3.3×10⁹ cells/m².

At various times before and after the infusions, samples of peripheral blood were tested for the presence of hygromycin-resistant HIV(gag)-specific CTLs using the chromium release assay as described in Example 8.

In particular, PBL obtained before adoptive immunotherapy (pre #1), 14 days after the first T cell infusion (14 days post #1), and 1 day after the second T cell infusion (1 day post #2) were stimulated in vitro with UV inactivated vac/gag infected monocytes. Cultures were restimulated after 6–8 days and then split into two aliquots and fed with media containing low concentrations of IL-2 (2–5 U/ml). One aliquot of the cultures also received hygromycin at a concentration of 300 micrograms/ml. After in vitro expansion, the T cells from these cultures were counted and assayed for cytolytic activity against autologous and MHC-mismatched target cells either mock infected, infected with vac/gag or infected with a control vac recombinant expressing CMV gB. The lytic activity against MHC-mismatched targets was always less than 10% and is not shown. The effector to target ratio for the data shown is 10:1 except for the Pre #1+Hygro culture in which too few viable cells were counted to achieve an E/T of 10:1. For this effector, the entire culture was assayed.

Figure 15:
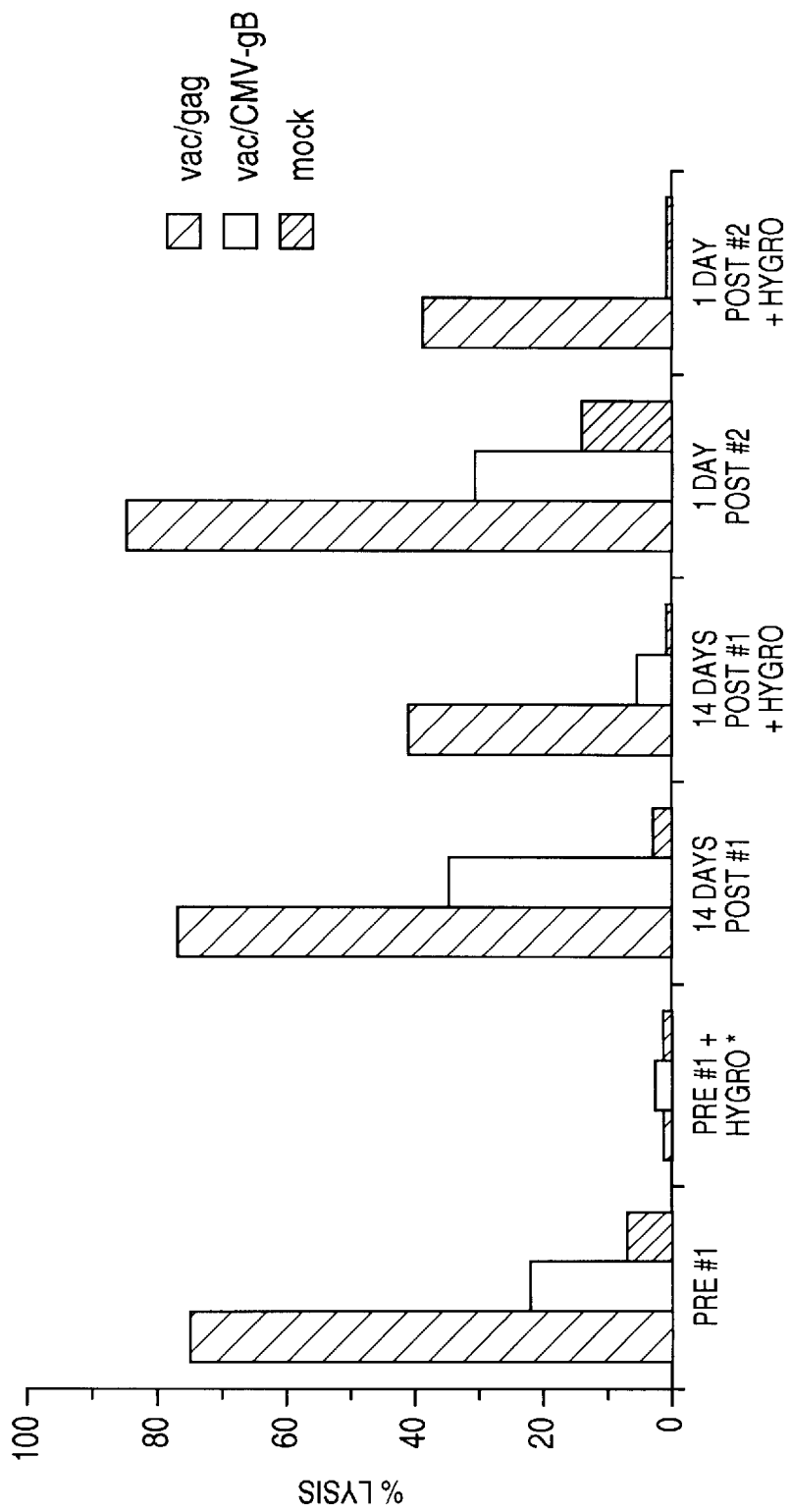
FIG. 15 is an illustration of data demonstrating adoptive immunotherapy using genetically-transduced antigen-specific CTL, as described in Example 19.

The data, shown in FIG. 15, indicate the presence of endogenous gag-specific cytolytic activity in the pre #1 culture which is abrogated by the addition of hygromycin B; whereas hygromycin resistant gag-specific CTL activity persists in the cultures initiated from PBL obtained 14 days after the first infusion and 1 day after the second infusion. The retention of the transferred cells was also confirmed by PCR of DNA extracted from peripheral blood mononuclear cells.

These results demonstrate the successful adoptive transfer of antigen-specific cytotoxic T lymphocytes that had been genetically modified and then rapidly expanded using the methods of the present invention.

We claim:

1. A method for expanding an initial T lymphocyte population in culture medium in vitro, comprising the steps of: adding an initial T lymphocyte population comprising at least 10⁴ T lymphocytes to a culture medium in vitro; adding to the culture medium a disproportionately large number of non-dividing peripheral blood mononuclear cells (PBMC) as feeder cells such that the resulting population of cells contains at least about 40 PBMC feeder cells for each T lymphocyte in the initial population to be expanded; adding non-dividing EBV-transformed lymphoblastoid cells (LCL) as feeder cells; adding anti-CD3 monoclonal antibody and IL-2 to the culture medium; and incubating the culture, thereby producing an expanded population of antigen specific, MHC-restricted T lymphocytes.

2. The expansion method of claim 1, wherein the initial T lymphocyte population comprises at least one human CD8+ antigen-specific cytotoxic T lymphocyte.

3. The expansion method of claim 1, wherein the non-dividing PBMC feeder cells comprise gamma-irradiated PBMC feeder cells.

4. The expansion method of claim 1, wherein the ratio of PBMC feeder cells to initial T lymphocytes is at least about 200:1.

5. The expansion method of claim 4, wherein the ratio of PBMC feeder cells to initial T lymphocytes is between about 400:1 and 800:1.

6. The expansion method of claim 1, wherein the ratio of LCL feeder cells to initial T lymphocytes is at least about 10:1.

7. The expansion method of claim 6, wherein the ratio of LCL feeder cells to initial T lymphocytes is between about 50:1 and 200:1.

8. The expansion method of claim 1, wherein the concentration of anti-CD3 monoclonal antibody is at least about 0.5 ng/ml.

9. The expansion method of claim 1, wherein the concentration of anti-CD3 monoclonal antibody is at least about 1.0 ng/ml.

10. The expansion method of claim 1, wherein the concentration of Il-2 is at least about 10 units/ml.

11. The expansion method of claim 10, wherein the incubation is continued for at least about 9 days and wherein the step of adding IL-2 to the culture medium is repeated after each 3–5 day interval.

* * * * *